United States Patent
Ottoboni et al.

(10) Patent No.: US 8,721,641 B2
(45) Date of Patent: May 13, 2014

(54) EXTERNAL ORTHOPAEDIC FIXATOR FOR THE ELBOW JOINT

(75) Inventors: Andrea Ottoboni, Rovigo (IT); Daniele Venturini, Povegliano Veronese (IT)

(73) Assignee: Orthofix S.r.l. (IT)

( * ) Notice: Subject to any disclaimer, the term of this patent is extended or adjusted under 35 U.S.C. 154(b) by 14 days.

(21) Appl. No.: 13/365,573

(22) Filed: Feb. 3, 2012

(65) Prior Publication Data

US 2012/0209266 A1    Aug. 16, 2012

Related U.S. Application Data

(60) Provisional application No. 61/442,018, filed on Feb. 11, 2011.

(51) Int. Cl.
| A61B 17/00 | (2006.01) |
| A61F 4/00 | (2006.01) |
| A61F 5/04 | (2006.01) |

(52) U.S. Cl.
USPC .............................................. 606/59; 606/54

(58) Field of Classification Search
USPC .............. 606/54–59, 53, 86 R, 87–91, 96–98
See application file for complete search history.

(56) References Cited

U.S. PATENT DOCUMENTS

| 3,985,127 | A | * | 10/1976 | Volkov et al. ................... | 606/90 |
| 4,604,997 | A | * | 8/1986 | De Bastiani et al. ........... | 606/55 |
| 4,637,382 | A | * | 1/1987 | Walker ............................. | 606/55 |
| 5,100,403 | A | * | 3/1992 | Hotchkiss et al. .............. | 606/56 |
| 5,102,411 | A | * | 4/1992 | Hotchkiss et al. .............. | 606/57 |
| 5,328,446 | A | * | 7/1994 | Bunnell et al. .................. | 602/16 |
| 5,376,091 | A | * | 12/1994 | Hotchkiss et al. .............. | 606/55 |
| 5,683,353 | A | * | 11/1997 | Hamersly ........................ | 602/16 |
| 5,846,245 | A | * | 12/1998 | McCarthy et al. ............. | 606/105 |
| 5,897,555 | A |   | 4/1999 | Clyburn et al. | |
| 6,152,925 | A | * | 11/2000 | Marsh et al. .................... | 606/54 |
| 6,355,037 | B1 | * | 3/2002 | Crosslin et al. ................. | 606/57 |
| 6,409,729 | B1 | * | 6/2002 | Martinelli et al. .............. | 606/59 |
| 6,520,961 | B1 |   | 2/2003 | Marsh | |
| 7,326,212 | B2 | * | 2/2008 | Huebner ........................ | 606/328 |
| 7,449,023 | B2 | * | 11/2008 | Walulik et al. ................. | 606/59 |
| 2006/0155276 | A1 | * | 7/2006 | Walulik et al. ................. | 606/59 |
| 2006/0229604 | A1 | * | 10/2006 | Olsen et al. ..................... | 606/54 |
| 2009/0024128 | A1 |   | 1/2009 | Nakamura et al. | |
| 2009/0228006 | A1 | * | 9/2009 | Mussolin ........................ | 606/59 |
| 2012/0029398 | A1 | * | 2/2012 | Bonutti et al. .................... | 601/5 |
| 2012/0179273 | A1 | * | 7/2012 | Clifford et al. ................. | 623/46 |

OTHER PUBLICATIONS

International Search Report issued in connection with PCT/EP2011/004551.

* cited by examiner

*Primary Examiner* — Ellen C Hammond
*Assistant Examiner* — Jacqueline Johanas
(74) *Attorney, Agent, or Firm* — Akerman LLP

(57) ABSTRACT

An external orthopaedic fixator for elbow joints comprising: proximal anchoring means intended to be integrally associated to a proximal bone of a patient's upper limb; distal anchoring means intended to be integrally associated to a distal bone of a patient's upper limb; an articulator hinging together said proximal and distal anchoring means along a hinging axis, intended to be positioned in correspondence with an elbow joint connecting said proximal and distal bones; said articulator comprising a radiotransparent centering window intended to frame the elbow joint when positioning the external orthopaedic fixator, said hinging axis passing through said centering window.

11 Claims, 16 Drawing Sheets

EXTERNAL ORTHOPAEDIC FIXATOR FOR THE ELBOW JOINT

CROSS-REFERENCE TO RELATED APPLICATIONS

This application claims priority to U.S. Provisional Patent Application No. 61/442,018 filed Feb. 11, 2011, the disclosure of which is hereby incorporated by reference.

FIELD OF APPLICATION

The present invention applies to the field of orthopaedic surgery and it concerns a device for the treatment of fractures and articular rigidity of the elbow joint.

In particular, the device is an articulated external fixator of the type comprising a proximal portion and a distal portion, intended to be associated respectively to a humerus and an ulna of a patient's upper limb, being hinged to each other by means of an articulator arranged in correspondence with the elbow joint.

PRIOR ART

Flexion contracture of the joints due to the treatment of elbow joint trauma or other causes (inflammations, burns, arthritis), assumes particular clinical importance in terms of frequency and extent of the disablement.

In fact, even minor contractures (about)30°-40° considerably reduce upper limb functionality. In many cases the recovery of mobility after the contracture, by means of rehabilitation or distraction arthroplasty, can be limited or prohibited by pain and/or swelling, with relevant muscle tendon shortening on both sides of the joint.

Some techniques like early active motion, general therapy, continuous passive motion (CPM), can be used to confront the problem, but they do not in any sure way guarantee that the problem will be resolved.

Early active motion may reduce the gravity of the contracture, but it requires constant and taxing commitment on the part of the patient.

In general therapy, passive stretching performed with the help of a therapist can cause heterotopic bone formation and ossifying myositis.

Finally, CPM devices allow quick recovery of mobility, but they do not reach the ends of the kinematic movement, which is where the need for rehabilitation is greatest.

From the above it is clear that there exists a need for external fixators for elbow joints, which, besides allowing the joint to be protected in case of fracture or instability, also allow the joint to be distracted for rehabilitation purposes.

These fixators must allow the elbow joint to move both actively and passively, reproducing the entire kinematic movement usually allowed by a healthy joint and promoting soft tissue extension in the end positions of flexion and extension.

At present, there are only a few orthopaedic devices that meet these requirements, with limited effectiveness.

In fact, articulated external fixators on the market are not specifically designed for the rehabilitation of joint rigidity and therefore they have a series of drawbacks that make them unsuitable for the purpose.

A first drawback derives from the difficulty of centering and repositioning the external fixator with respect to the elbow joint. In fact, this centering is hindered both by radiopaque fixator components that reduce bone joint visibility, and by the difficulty in identifying the device's hinging axis.

Another drawback derives from the fact that external fixators on the market do not allow a complete kinematic movement of the elbow joint to which they are associated.

A further drawback is due to the excessive size and weight of the external elbow joint fixators known today.

The technical problem underlying the present invention is therefore to provide an external orthopaedic device for elbow joints that solves one or more of the above-mentioned drawbacks and that is as suitable as possible for resolving joint rigidity.

SUMMARY OF THE INVENTION

The above-mentioned technical problem is solved by an external orthopaedic fixator for elbow joints comprising: proximal anchoring means intended to be integrally associated to a proximal bone of a patient's upper limb; distal anchoring means intended to be integrally associated to a distal bone of a patient's upper limb; an articulator that hinges said proximal and distal anchoring means along a hinging axis, intended to be positioned in correspondence with an elbow joint that connects said proximal and distal bones, where the articulator comprises a radiotransparent centering window intended to frame the elbow joint when positioning the external orthopaedic fixator, said hinging axis passing through said centering window.

It is clear also to someone not skilled in the art that the presence of the radiotransparent window considerably helps in the step of centering the joint axis, which is generally recognized as the most critical step of the intervention for implanting the orthopaedic fixator.

Further assistance in the centering step comes from radiopaque references in the centering window that guide the centering of the elbow joint.

Moreover, this centering window can advantageously comprise a central tube oriented along the hinging axis, to allow for the possible insertion of a reference wire of the known type, such as, for example, a Kirschner wire.

Proximal anchoring means can comprise at least one proximal rod connected to the articulator and fixed to the proximal bone by means of proximal endosseous pins supported by at least one proximal clamp.

In a particularly advantageous embodiment, said proximal clamp comprises a first coupling element arranged to lock proximal endosseous pins, and a second coupling element arranged to lock the proximal rod, these coupling elements being articulated with each other by means of an articulation pin that comprises a head associated to the first coupling element and a shank associated to the second coupling element.

Thus the second coupling element may be selectively rotatable around the axis of the articulation pin. Selectively rotatable means that the rotation can advantageously be blocked if necessary. For example, a ring nut can be used, associated to the threaded end of the shank of the articulation pin and intended to push, by fastening, the second coupling element against the first coupling element, thereby preventing its relative rotation.

Moreover the head of the articulation pin can advantageously have a through-hole through which an axis passes that is transverse to the first coupling element, so that said articulation pin is selectively rotatable with respect to said transverse axis. In this case too, the expression "selectively rotatable" indicates the possibility of blocking this rotation if need be. To this purpose, it is possible to use the same ring nut that also blocks the rotation of the second coupling element with respect to the axis of the articulation pin. Moreover, said transverse axis can be defined by a fixing eccentric that makes a further degree of approach between the first and second coupling elements possible, thus locking the joint more tightly between the elements of the proximal clamp.

Said transverse axis is preferably perpendicular to the axis of the articulation pin and parallel to the fixing axis of said proximal endosseous pins, so that these endosseous pins have a great range of orientational possibilities at their disposal.

The above-mentioned anchoring means can comprise at least one distal rod connected to the articulator and fixed to the distal bone by means of distal endosseous pins.

These distal endosseous pins can be supported by at least one distal clamp associated to the distal rod, which can advantageously allow three degrees of freedom between the rod and the pin (typically due to the ability of the rod to slide axially in its seat, the ability of the pin to slide axially in its seat and to the possibility of angular adjustment between the coupling elements locking the rod and the pin).

Alternatively, the distal endosseous pins can be supported directly by the distal rod and kept in position by means of locks fastened to the distal rod through fixing means (for example fixing screws). The distal rod and the locks can have opposite hollows that work together to define the seats of the distal endosseous pins.

This solution presents the advantage of clear structural cost reduction, at the price however of a lower operational flexibility, since the characteristic degree of rotational freedom of coupling elements forming a clamp must be abandoned.

It is clear that the solutions described above, with specific reference to the distal and proximal anchoring of the external orthopaedic fixator, should be taken as generally advantageous solutions, so that it is certainly possible to apply one of the distal solutions to the proximal anchoring and vice versa.

The articulator identified above can comprise a proximal joining portion integral with anchoring means and a distal joining portion integral with distal anchoring means.

The centering window may have a cylindrical geometry and define a hinging pin between the proximal joining portion and the distal joining portion.

In particular, one of said proximal or distal joining portions can then comprise at least one hinging ring that is rotatably slidable on an external cylindrical periphery of this centering window, said centering window being integral with the other joining portion.

The above-described solution realizes a hinge in a low-cost and effective way, ensuring the radiotransparency of the central element that is to be aligned with the elbow joint.

The articulator can advantageously comprise joint locking means arranged to block the relative rotation between the proximal joining portion and the distal joining portion. In particular, these means can take the form of a joint-locking screw.

The articulator can further comprise joint distraction means arranged to allow a translation of the distal anchoring means with respect to the proximal anchoring means.

These means are extremely advantageous in recuperation from joint rigidity in particular by means of distraction.

The above-mentioned translation preferably occurs along a distraction axis that is inclined by an angle of distraction with respect to the longitudinal axis of the distal bone, said angle of distraction being comprised between 60° and 75° (preferably 66°).

The distal joining portion defined above may comprise a coupling element hinged to the proximal joining portion and a distal connector integral with distal anchoring means, this distal connector being slidably movable with respect to said coupling element. In this case the joint distraction means may be arranged to create a translation of the distal connector with respect to the coupling element.

The distal connector can comprise a sliding arm that is slidably inserted in a sliding seat of the coupling element, said joint distraction means then having the form of a screw for distraction control, comprising a head rotatably associated to the sliding seat and a shank engaged in the sliding arm.

The distal connector can comprise a distal connection arm intended to longitudinally house a distal rod of the distal anchoring means, the subtended angle between the sliding arm and the distal connection arm being comprised between 105° and 120° (preferably 114°), so as to realize the angle of distraction defined above.

The fixator can further comprise distraction blocking means arranged to block the relative translation between the distal anchoring means and the proximal anchoring means. These means preferably take the form of a distraction blocking screw intended to fasten the two opposed edges that define the sliding seat of said sliding arm.

The external orthopaedic fixator according to the present invention can further advantageously comprise an auxiliary device that can be coupled to the articulator and that allows the relative rotation between the proximal and distal joining portions to be micrometrically adjusted.

The auxiliary device can comprise a box-shaped body, a rotatable portion (preferably plate-like) that is rotatably associated to said box-shaped body and fixing means intended to fix the box-shaped body and the rotating portion to the proximal joining portion and to the distal joining portion respectively, or vice versa. This box-shaped body comprises a mechanical reduction gear wheel intended to transmit a rotational movement from a control member to a rotating portion.

In particular, the mechanical reduction gear wheel can comprise a toothed wheel and a worm screw.

Moreover, this auxiliary device can be advantageously configurable according to two alternative configurations: a first configuration wherein said rotating portion is coupled to said control member by means of said mechanical reduction gear wheel; and a second configuration wherein said rotating portion is idle with respect to said control member.

In particular, in a first embodiment of the device, a drum can make said rotating portion integral with said toothed wheel, the group formed by said rotating portion, drum and toothed wheel being axially translatable between: a position corresponding to the first configuration of the auxiliary device, in which the toothed wheel engages the worm screw, and a position corresponding to the second configuration of the auxiliary device, in which the toothed wheel does not engage the worm screw.

In a second embodiment of the device a drum integral with the toothed wheel may be selectively coupled to the rotating portion by means of at least one limitation peg.

The auxiliary device further comprises means for selectively limiting the angular travel allowed between the box-shaped body and the rotating portion. The expression "selectively limiting" means that this limitation is not ineluctably due to morphological features of the device, but it can be suitably changed according to user's needs.

The means for selectively limiting the angular travel allowed between the box-shaped body and the rotating portion can be set to define both a lower limit and an upper limit of said angular travel.

In particular said means for selectively limiting the angular travel allowed between the box-shaped body and the rotating portion can comprise a plurality of limitation holes on the rotating portion and intended to house at least one limitation peg interacting with limit stops of the box-shaped body.

In the second embodiment of the auxiliary device, the peg may advantageously be the one employed to selectively couple the drum to the rotating portion.

The above-described auxiliary device grants several advantages to the external orthopaedic fixator according to the present invention.

In fact, it makes it possible to perform a controlled micrometric joint movement, to limit the joint to the desired angle of movement according to preference and even to apply a constant torsion load continuous in time to be applied in any joint position.

The external orthopaedic fixator according to the present invention can be provided inside a kit further comprising at least one distraction device to perform a joint distraction before implanting the fixator.

This distraction device comprises a distal clamp equipped with a fixed portion that can be associated to the patient's distal bone at the elbow joint and a moving portion that can be associated to proximal anchoring means, said moving portion being telescopically translatable with respect to said fixed portion.

The distraction device is advantageously shaped so as to create a centering window that frames the elbow joint when positioning the distraction device itself.

In particular, this centering window of the distraction device can be advantageously realized by opposed hollows of the fixed portion and of the moving portion of the distal clamp.

Further features and advantages will become apparent from the following detailed description of a number of preferred, but not exclusive, embodiments of the present invention, with reference to the attached drawings, given by way of non-limiting examples.

DETAILED DESCRIPTION

Figure 1:
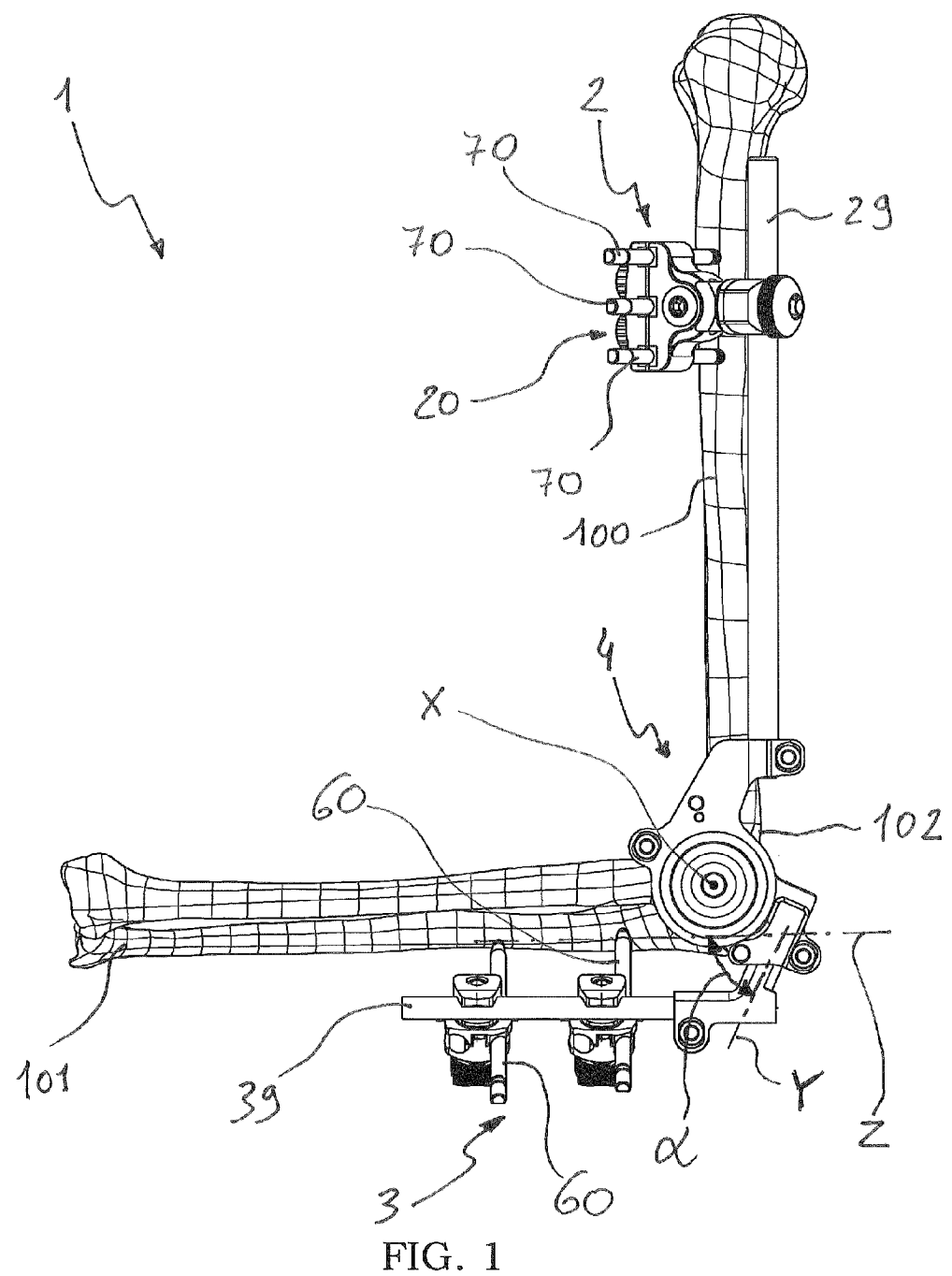
FIG. 1 is an axonometric view of an external orthopaedic fixator according to the invention associated to an elbow joint.
Figure 2:
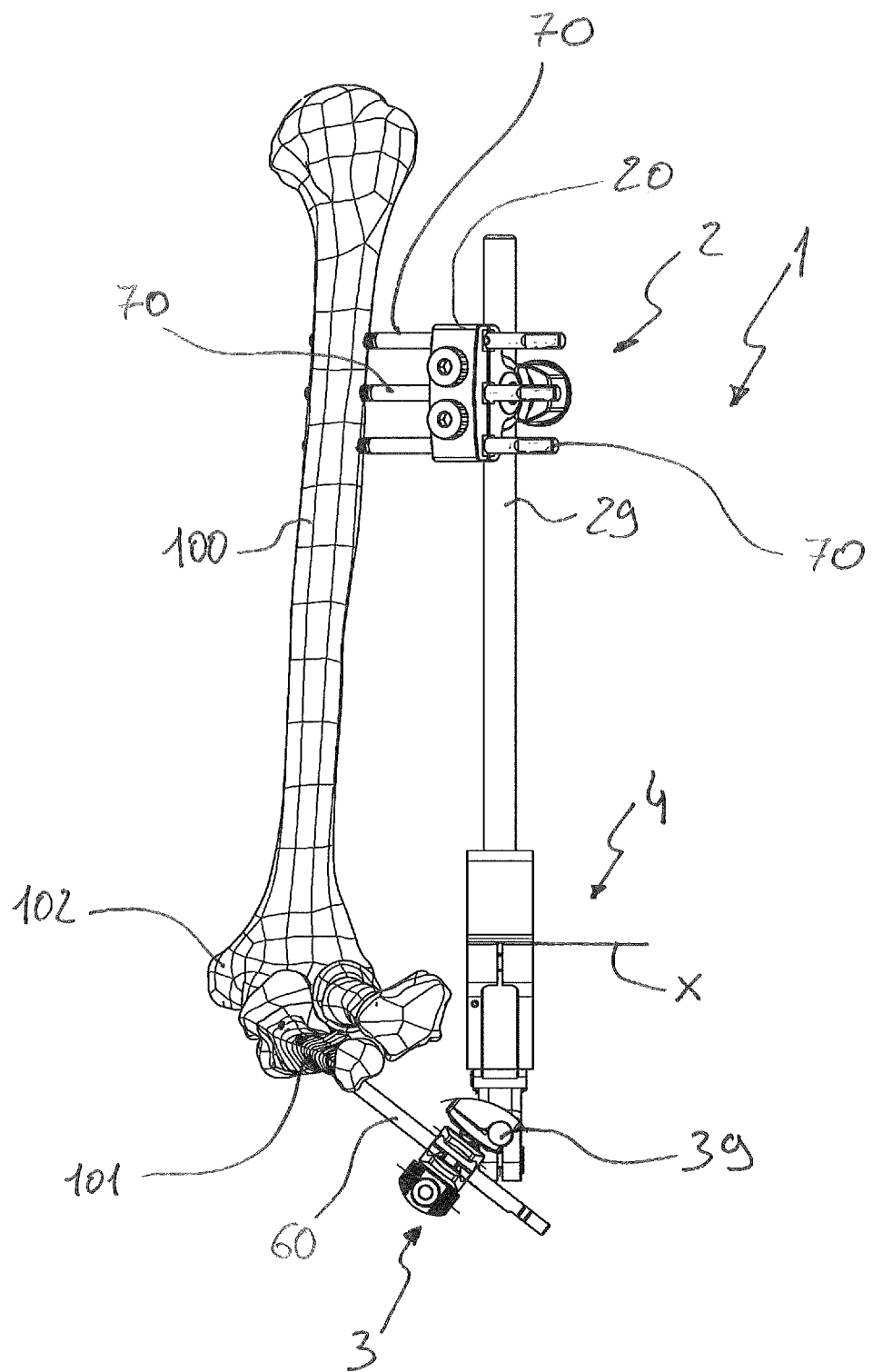
FIG. 2 is an axonometric view, according to a different perspective, of the external orthopaedic fixator of FIG. 1.
Figure 3:
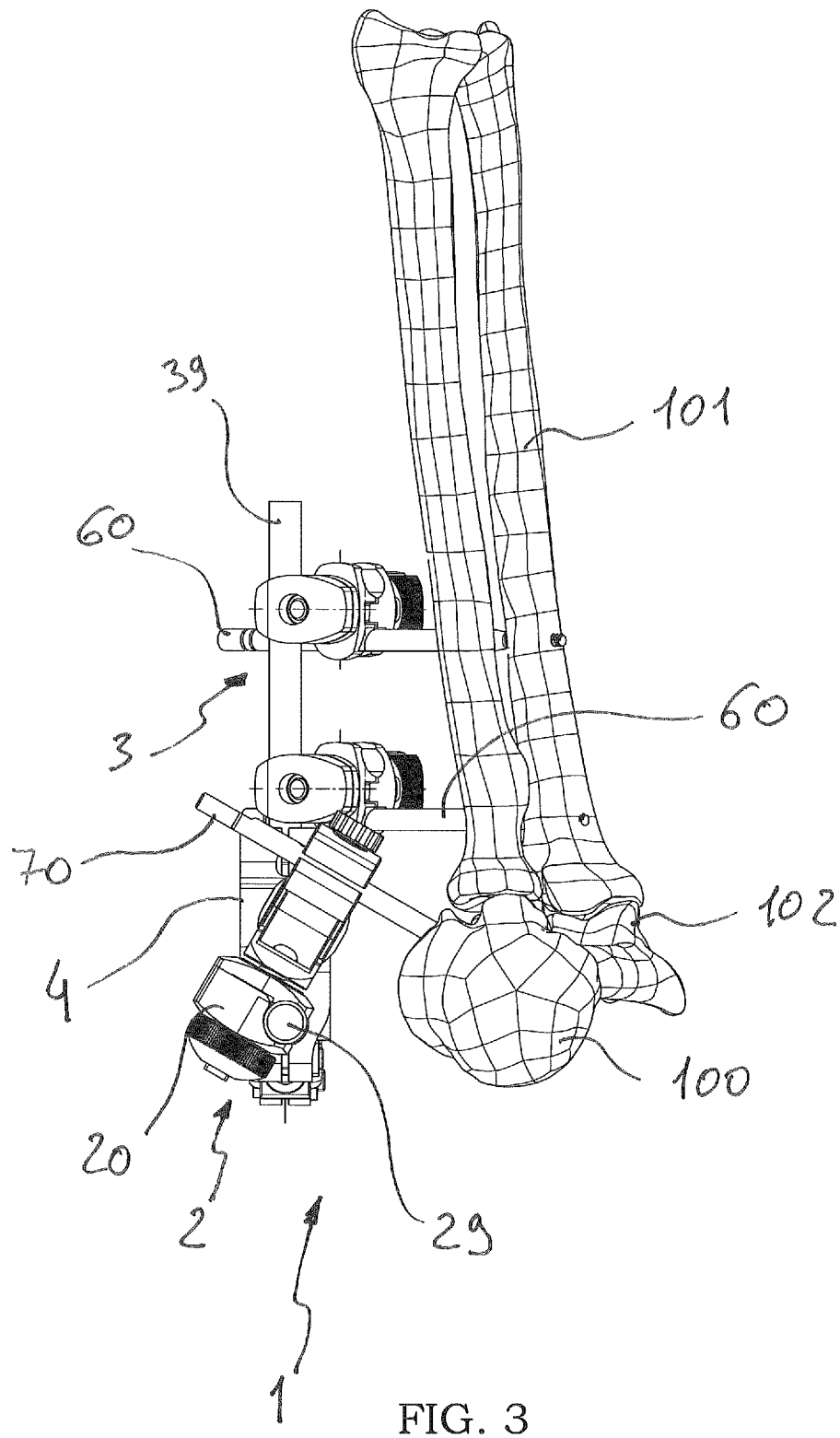
FIG. 3 is an axonometric view, according to a further different perspective, of the external orthopaedic fixator of FIG. 1.

With reference to the attached drawings, and particularly to FIGS. 1-3, an external orthopaedic fixator for elbow joints has been identified with reference number 1.

The device, as stated above, can be used for the treatment of traumas as well as articular rigidity concerning this joint.

The external orthopaedic fixator 1 comprises proximal anchoring means 2, intended to be integrally associated to the humerus 100 of the patient and distal anchoring means 3 intended to be integrally associated to the ulna 101.

The external orthopaedic fixator 1 further comprises an articulator 4 that hinges the proximal connector 2 to the distal connector 3 along a hinging axis x; when fixed on the patient, said articulator 4 is arranged in correspondence with the elbow joint 102, theoretically with the hinging axis x coinciding with the axis of rotation of said joint.

It must be noted that the external orthopaedic fixator 1 according to the preferred embodiment described here is of the monolateral type, i.e. the device structure, composed of proximal and distal anchoring means 2, 3 and of the articulator 4 joining them, only proceeds along one side of the sagittal plane passing through the elbow joint.

The proximal anchoring means 2 comprise a proximal rod 29 coupled to the articulator 4 at one of its ends and a proximal clamp 20 intended to anchor, by means of proximal endosseous pins 70, the proximal rod 29 to the patient's humerus 100.

Figure 4:
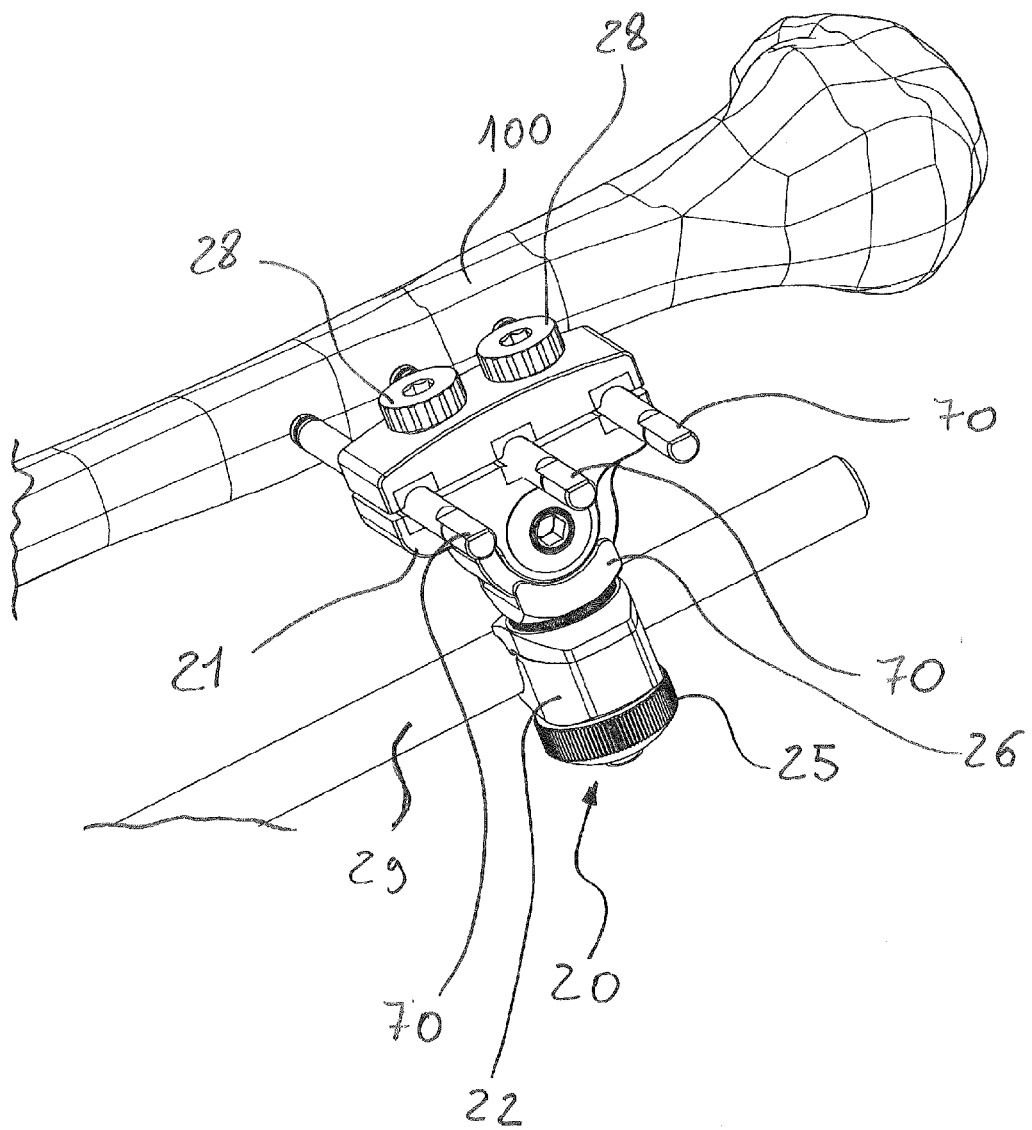
FIG. 4 is an axonometric view of a detail of the external orthopaedic fixator of FIG. 1.
Figure 5:
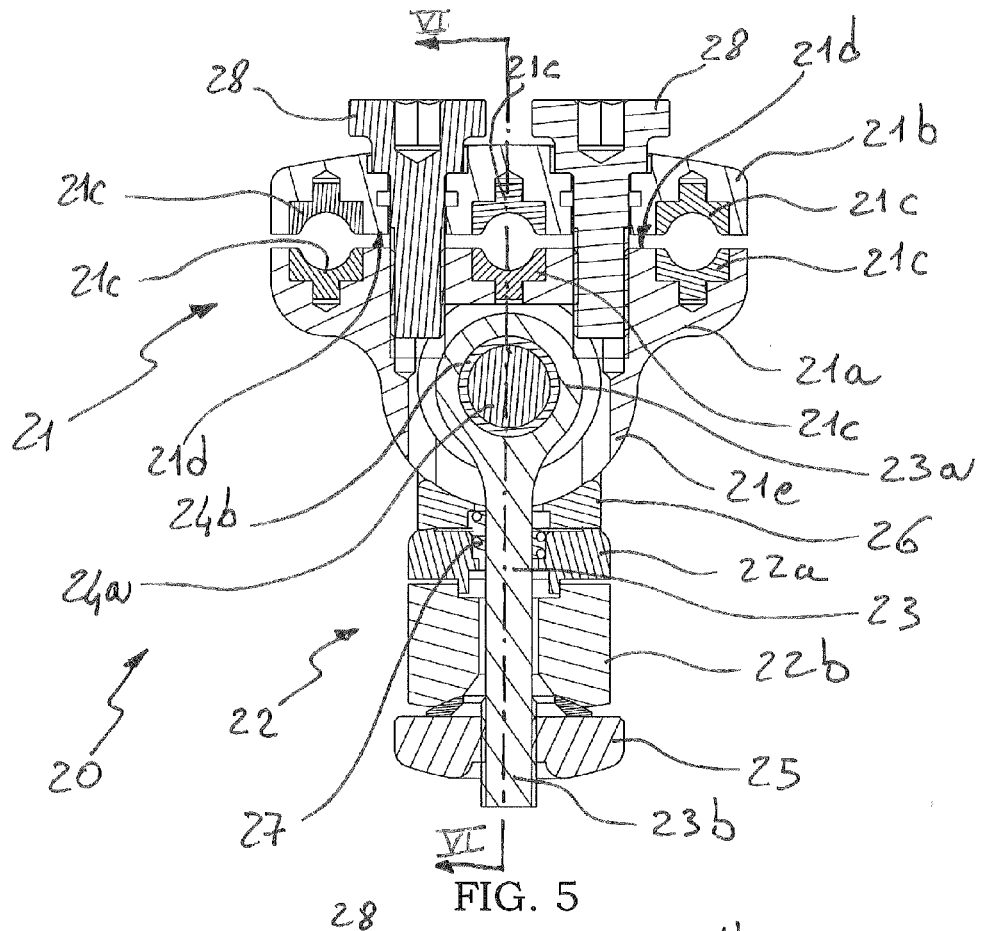
FIG. 5 is a sectional view of an element of the detail of FIG. 4.
Figure 6:
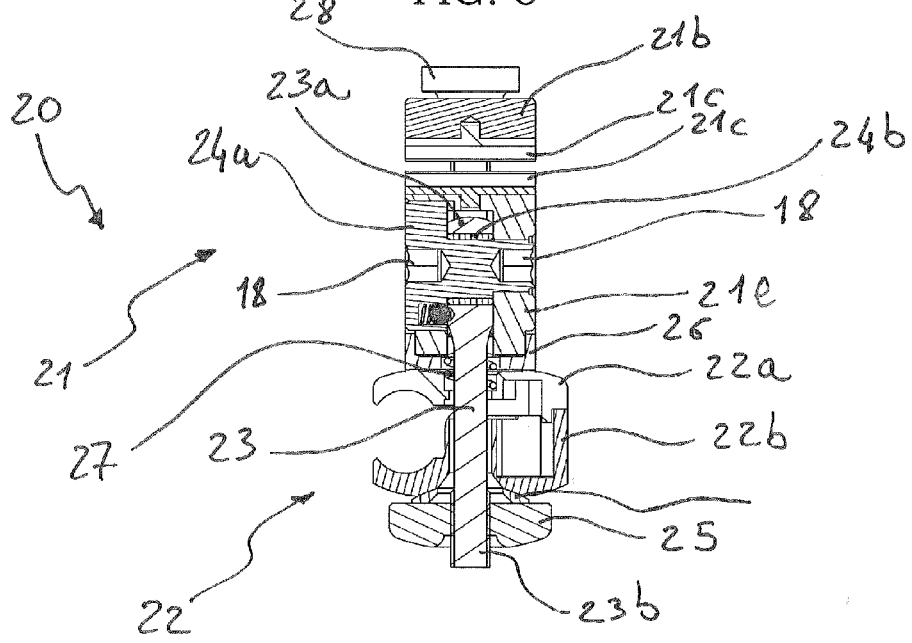
FIG. 6 is a view of the element of FIG. 5 sectioned along the plane VI-VI here defined.

The proximal clamp 20, which can be seen in detail in FIGS. 4-6, comprises a first coupling element 21 for the locking of proximal endosseous pins 70, and a second coupling element 22 for the locking of the proximal rod 29 instead.

The two coupling elements are connected together by means of an articulation pin 23, with a head 23a associated to the first coupling element 21 and a shank 23b associated to the second coupling element 22.

The first coupling element 21 comprises a first jaw 21a and a second jaw 21b, which are coupled together to define three through-seats to house as many proximal endosseous pins 70.

The second jaw 21b performs the function of lid and has a pair of through-holes that are at least partially threaded, for the passage of closing, screws 28. The first jaw 21a comprises a corresponding pair of blind holes that are internally threaded to receive by screwing the ends of the two screws 28.

In particular, the through-seats for housing the proximal endosseous pins 70 are defined by six non-conductive inserts 21c set into the body of the two jaws, and particularly arranged in opposite pairs on flat abutting surfaces 21d belonging to the first 21a and second jaw 21b respectively. The inserts 21c define a concave hemicylindrical surface, so that the surfaces of the opposite inserts define the three circular-section through-seats intended to house the cylindrical shank of proximal endosseous pins 70. The three seats are aligned with each other, parallel and equidistant.

The first coupling element 21 extends between two planar parallel faces and it has an elongated part, through which the through-seats pass, and a protruding part 21e intended to house the head 23a of the articulation pin 23.

In particular, the elongated part of the first coupling element 21 is concurrently defined by the first jaw 21a and second jaw 21.b; the protruding part 21e is instead defined by the first jaw 21a, developing opposite to the abutting surface 21d thereof.

The head 23a of the articulation pin 23 is then housed in a housing of the protruding part 21e, while the pin itself extends distancing itself from the abutting surface 21d. The head 23a has a through-hole oriented perpendicularly to the planar faces of the jaw; through this through-hole passes a fixing eccentric 24a inserted in a bushing 24b. Said eccentric 24a presents on the two opposite sides accessible from the outside a respective hollow socket head 18 to receive a control socket wrench. The simple rotation of the eccentric 24a promotes a traction of the articulation pin 23 towards the first coupling element 21 of the proximal clamp 20.

The second coupling element 22 comprises an upper jaw 22a to which a lower jaw 22b is connected. The upper and lower jaws define a C-section intended to receive the proximal rod 29; moreover through their center the shank 23b of the articulation pin 23 passes, which is then inserted into the through-holes on the surfaces of the two opposite jaws.

The free end of the shank 23 of the articulation pin 23 is threaded, and a ring nut 25 is mounted on it, arranged to press the second coupling element 22 against the first element 21, at the same time fastening the jaws of the second coupling element 22.

An adapter 26 is conveniently interposed between the first coupling element 21 and the second coupling element 22, comprising a convex surface intended to slide on the external hemicylindrical surface of the first coupling element 21 and an opposite flat surface intended to abut against the external surface of the upper jaw 22a of the second coupling element 22.

A helical compression spring 27 is interposed between the adapter 26 and the upper jaw 22a of the second coupling element 22, surrounding the shank 23b of the articulation pin 23; this spring, countering the fastening action of the ring nut 25, is housed in apposite impressions on the upper jaw 22a of the second coupling element 22 and on the adapter 26 against which it abuts.

It should be noted that the proximal clamp 20 described above can alternately have a slack and a locked configuration. In the slack configuration, there is play between the coupling elements that together form the clamp so that: the second coupling element 22 is rotatably movable with respect to the first element 21 around the axis of the shank 23b of the articulation pin 23, which functions as a hinge; and the articulation pin 23 is free to rotate with respect to the first coupling element 21 around the axis of the fixing eccentric 24a, which functions as a hinge between the two elements. Starting from this configuration, by first manually rotating the ring nut 25, the first 21 and second 22 coupling elements are brought closer together against the force of the helical compression spring 27, then by rotating the fixing eccentric 24a a further approach of the elements is obtained in which the proximal clamp 20 is placed in the locked configuration. In the locked configuration the relative orientations between the first coupling element 21, the second coupling element 22 and the articulation pin 23 are blocked, so that the clamp becomes a monolithic whole.

The distal anchoring means 3 comprise a distal rod 39, 39" that is coupled to the articulator 4 and intended to be anchored, by means of distal endosseous pins 60, to the patient's ulna 101.

It should be noted that the point where the distal endosseous pins 60 are fixed to the ulna 101 is of crucial importance for several reasons.

First of all it is necessary that these pins are not inserted in a position that is too distal, since that could interfere with the line of movement of the radius when the patient's wrist rotates.

Secondly, insertion of the pin should be easy, so that it is preferable to implant in particular sites of the ulna that offer a flat surface for the drill.

Finally, it is better to avoid inserting pins on the ulna from the back, which would complicate the patient resting his or her elbow on a surface.

In order to meet the requirements stated above, different alternative embodiments for anchoring the distal endosseous pins 60 to the distal rod 39, 39", i.e. different types of distal anchoring means 3, are suggested hereafter.

The first two embodiments, which are particularly advantageous since they allow the pins to be arranged independently, provide the use of two distal endosseous pins 60 anchored to the distal rod 39 by means of two, distal clamps 30, 30' independent from each other.

Figure 7:
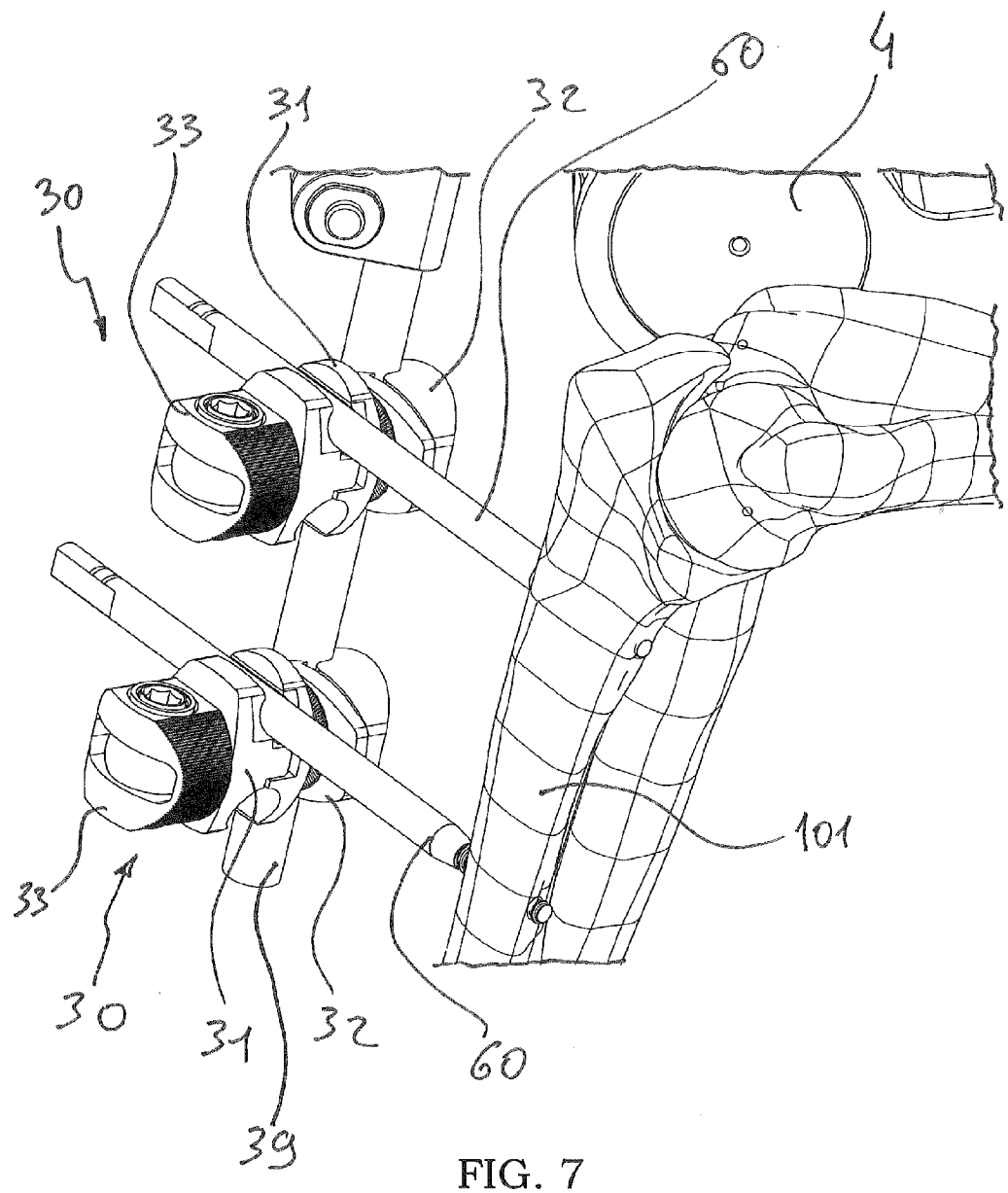
FIG. 7 is an axonometric view of a detail of the external orthopaedic fixator of FIG. 1.

In the first embodiment shown in FIG. 7, distal clamps 30 comprise a first coupling element 31 and a second coupling element 32 suitably connected by means of a fastening screw operated by a handle 33 and by a locking eccentric (not visible in the figures) integrated into the handle itself.

The first coupling element 31 is composed of two rigid portions that can be fastened to each other by means of the fastening screw; these rigid portions have side jaws defining two C-shaped side seats to receive the pins. By bringing the two rigid portions closer by means of the fastening screw, the jaws are clamped around the shank of a distal endosseous pin 60 potentially placed in one of the two C-shaped seats.

The second coupling element 32 comprises a main portion laterally defining a seat for housing the distal rod 39; and a secondary portion that covers the main portion and that locks the rod within this seat.

The first and second coupling elements 31, 32 are rotatably mounted with respect to each other on the connection screw when the latter is unfastened; when fastening the screw, the two coupling elements are pressed and kept against each other and relatively locked by projections that are respectively present on the two contact surfaces.

It should be noted that, before fastening the screw, the endosseous pins applied to the distal clamps 30 have three distinct degrees of freedom with respect to the distal rod 39: the first as a result of the fact that the clamps are free to slide along the rod, the second as a result of the relative rotation between the two coupling elements that compose the clamp, the third as a result of the axial sliding of the pin inside its seat.

Figure 11:
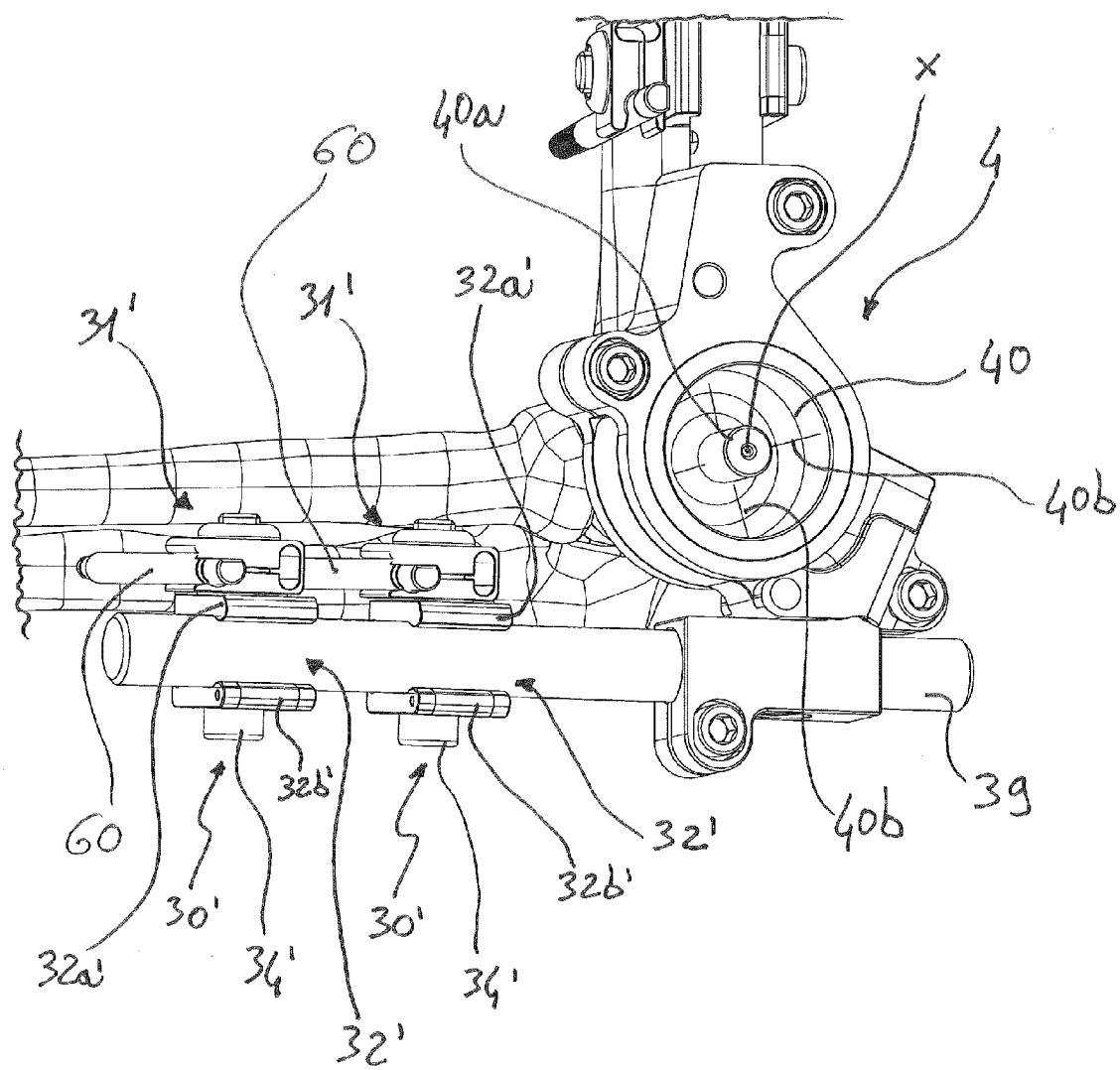
FIG. 11 is an axonometric view of a detail of an external orthopaedic fixator according to a different embodiment.
Figure 12:
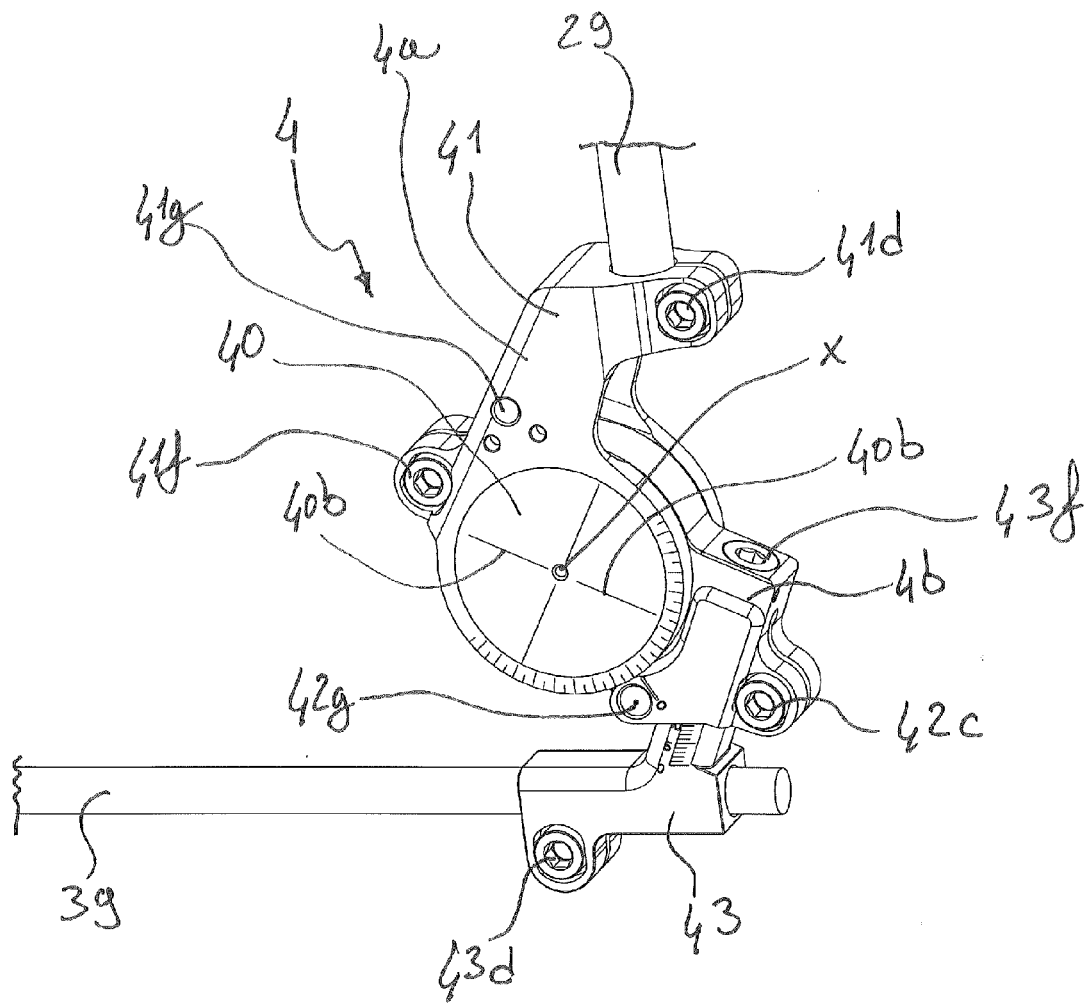
FIG. 12 is an axonometric view according to a different perspective of the detail of FIG. 11.
Figure 13:
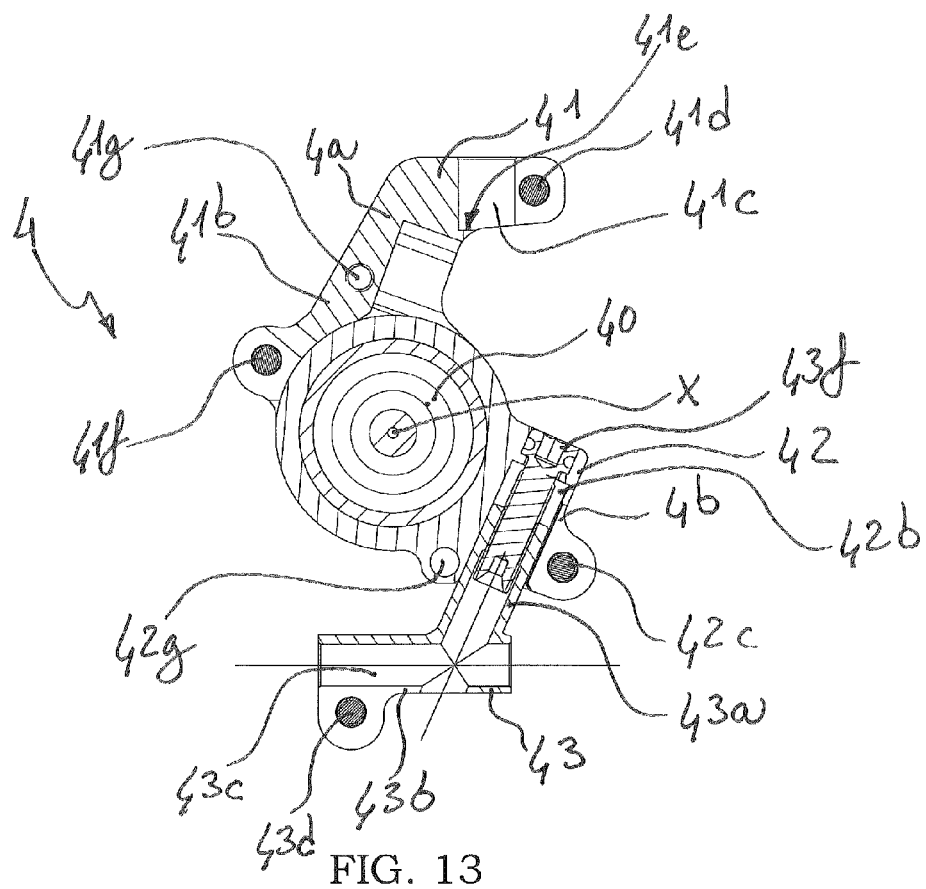
FIG. 13 is a sectional view of an element of the external orthopaedic fixator according to the invention.
Figure 14:
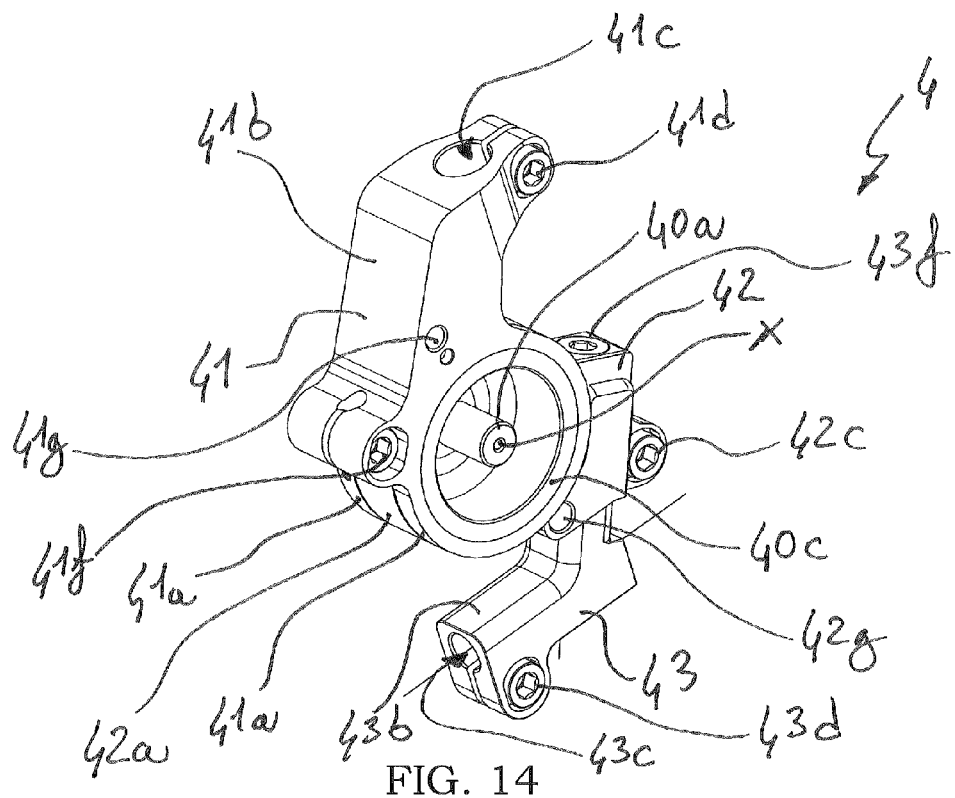
FIG. 14 is an axonometric view of the element of FIG. 13.
Figure 15:
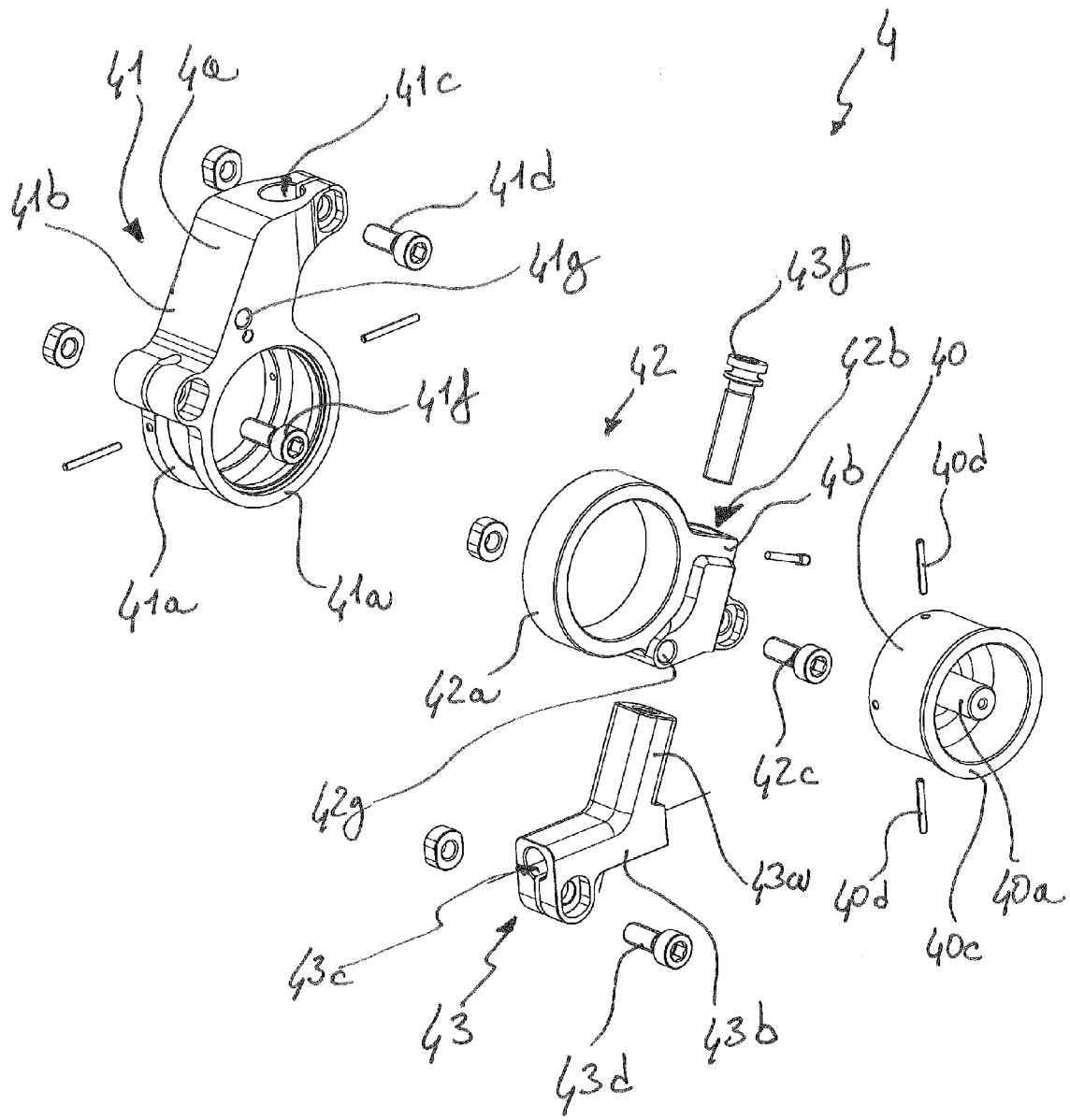
FIG. 15 is an exploded view of the element of FIG. 13.
Figure 16:
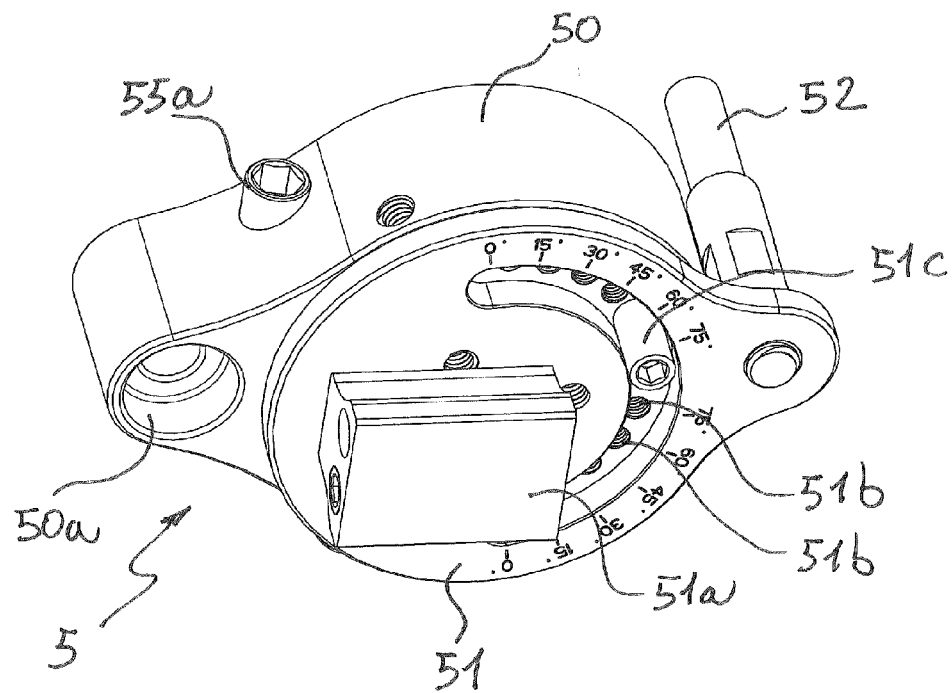
FIG. 16 is an axonometric view of an embodiment of an auxiliary device of the external orthopaedic fixator according to the invention.
Figure 17:
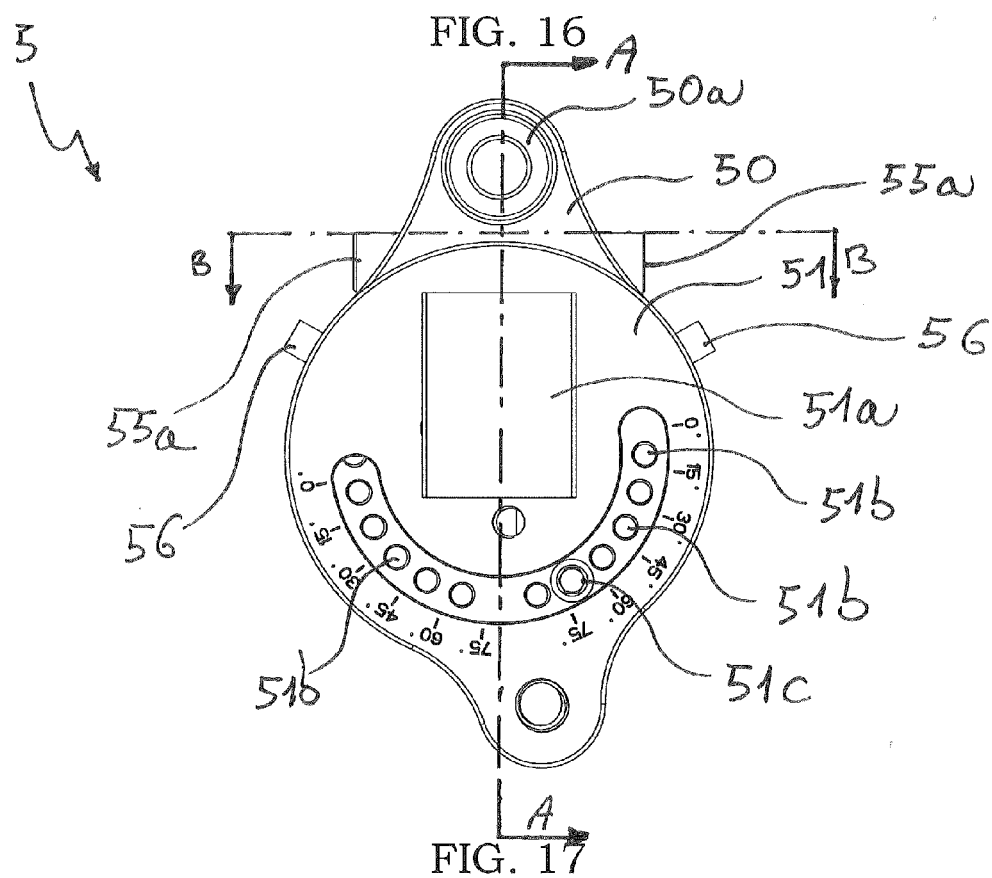
FIG. 17 is a plan view of the auxiliary device of FIG. 16.
Figure 18:
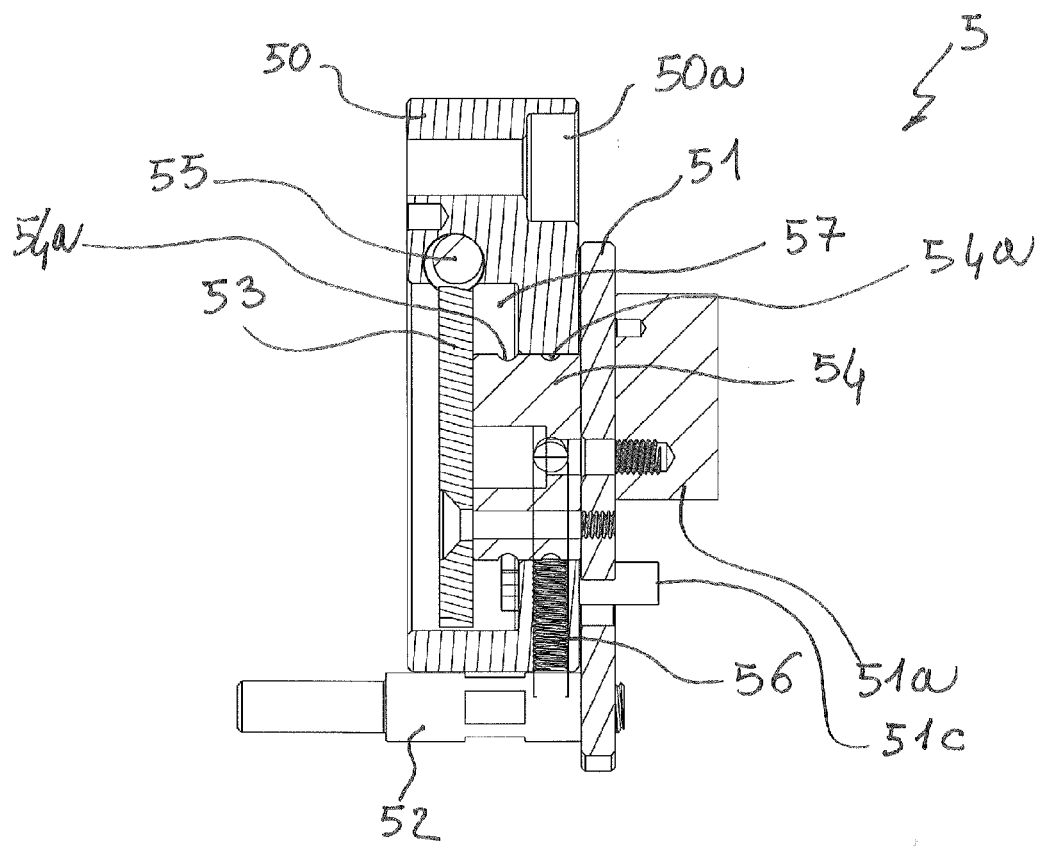
FIG. 18 is a view of the device of FIG. 16 sectioned along the plane A-A defined in FIG. 17.
Figure 19:
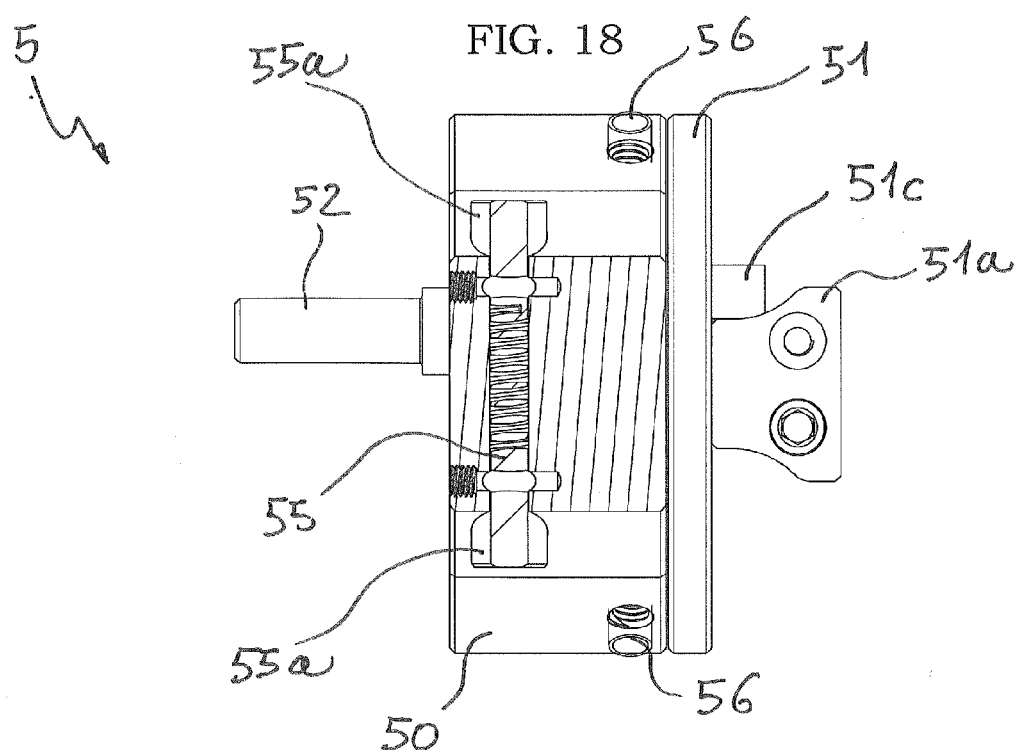
FIG. 19 is a view of the device of FIG. 16 sectioned along the plane B-B defined in FIG. 17.
Figure 20:
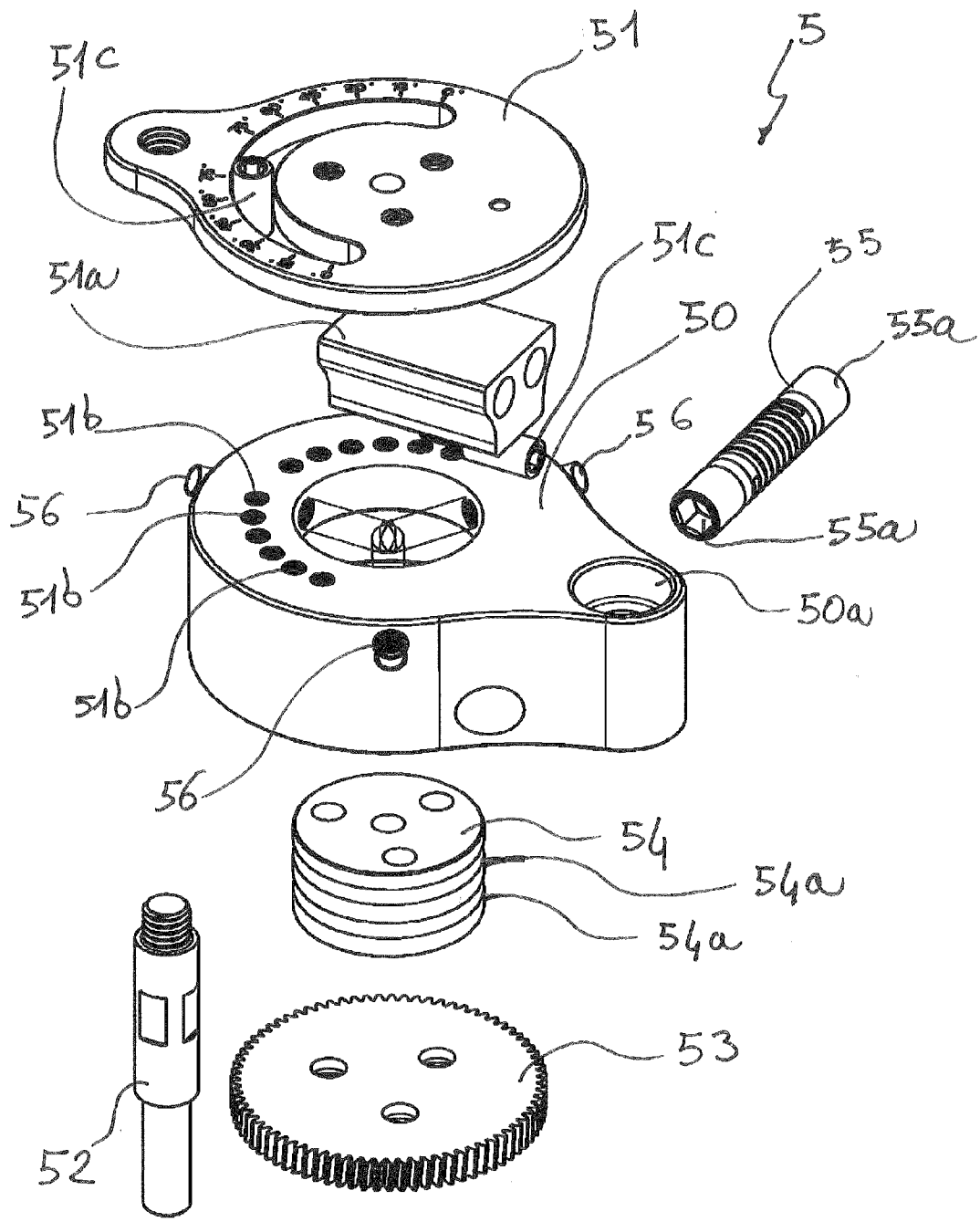
FIG. 20 is an exploded view of the device of FIG. 16.

A second manner of fixing distal endosseous pins 60 to the distal rod 39 involves the use of distal clamps 30' of a different shape, which can be seen in FIG. 11.

The distal clamps according to this embodiment comprise a first coupling element 31' and a second coupling element 32' opportunely connected by means of a fastening screw 34'.

The first coupling element 31' is composed of two opposite arms connected together by a flexible bridge, laterally defining a C-shaped seat for tightening a distal endosseous pin 60. Through these arms the fastening screw 34' passes, one end of which is screwed inside the outermost arm of the device. The other arm, instead, is in contact with the second coupling element 32'.

The second coupling element 32' comprises a fixed portion 32a' defining a C-shaped lateral seat for the distal rod 39, and a movable jaw 32b' hinged to the end of the outermost arm of the C-shaped seat. The tightening of the fastening screw 34' acts on the moving jaw 32b' in order to lock in position the distal rod 39 potentially placed in the C-shaped seat.

In this case too, the first and second coupling elements 31', 32' are rotatably mounted with respect to each other on the connection screw 34' when the latter is untightened; when tightening the screw, the two coupling elements are pressed and kept against each other and relatively locked by projections respectively arranged on the two contact surfaces.

It should be noted that, before tightening the screw, the endosseous pin applied to distal clamps 30' have three distinct degrees of freedom with respect to the distal rod 39: the first as a result of the fact that the clamps are free to slide along the rod, the second as a result of the relative rotation between the two coupling elements that compose the clamp, the third as a result of the axial sliding of the pin inside its seat.

In alternative to the embodiments described above comprising distal clamps 30, 30', it is possible to anchor distal endosseous pins 60 according to the following embodiments.

Figure 8:
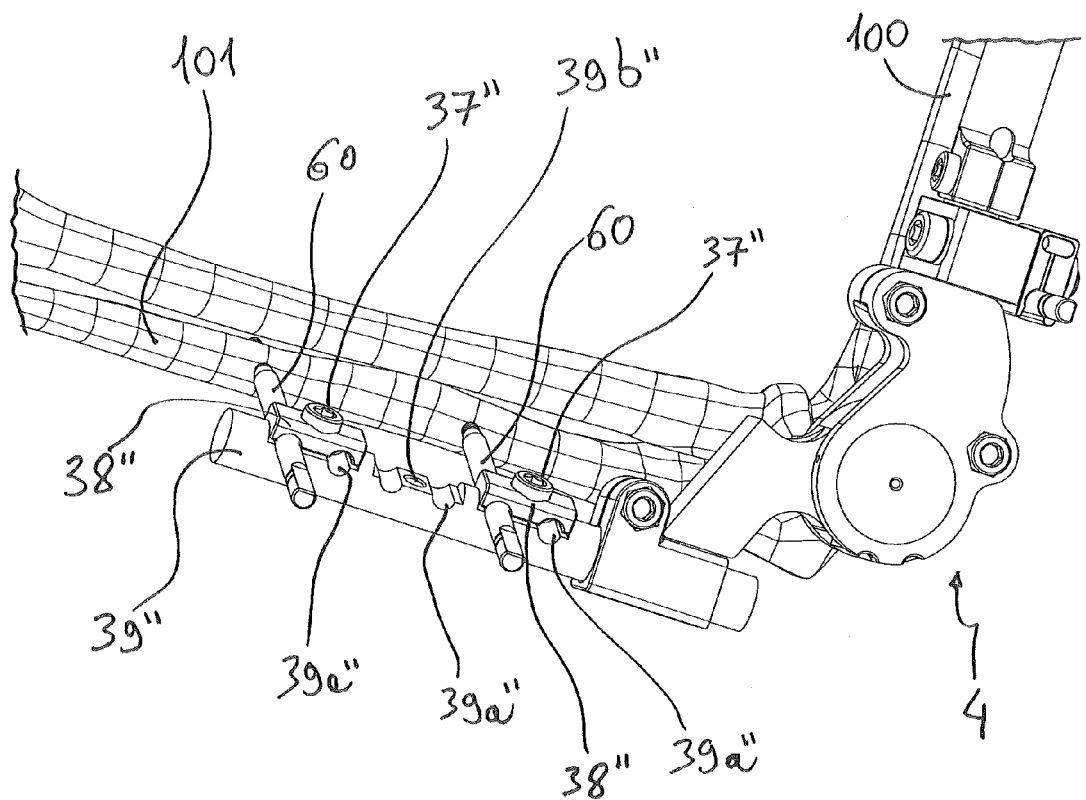
FIG. 8 is an axonometric view of a detail of an external orthopaedic fixator according to a different embodiment.

In a third embodiment, which can be seen in FIG. 8, the distal rod 39" has a plurality of planar impressions, with two hemicylindrical hollows 39a" opening on each of them. A threaded blind hole 39b" is realized between the two hemicylindrical hollows 39a" of each planar impression. Locks 38", which have a flat locking surface intended to abut against the profile of the impression, can be positioned above the planar impressions. The locking surface comprises two hemicylindrical hollows that are placed opposite the hollows of the impressions that define seats for the distal endosseous pins 60. The locks 38" have a hole into which a fixing screw 37" is inserted whose end engages the threaded blind hole 39b" of the impression below. By tightening the fixing screw 37" the distal endosseous pins 60 potentially placed in said seats are then locked.

The articulator 4, which can be seen in detail in the attached FIGS. 12-15, is composed of a proximal joining portion 4a, intended to fix the proximal rod 29, and of a distal joining portion 4b, intended to fix the distal rod 39, 39". The two joining portions 4a, 4b are rotatably mounted with respect to each other along the hinging axis x; when implanting the external orthopaedic fixator 1 the surgeon should ideally let this axis coincide with the axis of rotation of the elbow joint 102.

The proximal joining portion 4a comprises a centering window 40 and a proximal connector 41 integrally associated to it.

The centering window 40 is a cylindrical element defining, according to modes which will be illustrated hereafter, the hinging axis between the proximal 4a and distal 4b joining portions.

The centering window 40 is also intended to facilitate the centering of the hinging axis x with the elbow joint 102, which is the most critical part of the implanting intervention of the external orthopaedic fixator 1.

To achieve said aim, the centering window 40 is made of a radiotransparent material and its dimensions permit the elbow joint 102 to be framed during the positioning of the external orthopaedic fixator 1.

The centering window 40 comprises a central tube 40a oriented along the hinging axis x, to allow the potential insertion of a reference wire.

To facilitate the centering further, radiopaque references 40b are arranged on the radiotransparent circular surface of the centering window 40, in particular lines of sight that are orthogonal to the hinging axis x.

The centering window 40 has a cylindrical lateral surface with a shoulder edge 40c at its end; the opposite end instead provides four holes perpendicular to the cylindrical surface for the insertion of elastic fixing pegs 40d.

The proximal connector 41 comprises a proximal connection arm 41b, at an end of which two proximal hinging rings 41a extend that are essentially the same and parallel, whose function will be illustrated hereafter. Instead the opposite end of the proximal connection arm 41b has an insertion seat 41c for the proximal rod 29, composed of a hole defined between two fork-like appendices of the proximal connection arm 41b. The two appendices can be brought closer to each other by means of a proximal connection screw 41d. The end of the proximal rod 29, inserted into the insertion seat 41c, abuts against a projection 41e and it is locked in position by tightening the proximal connection screw 41d.

The proximal connector 41 shows, in correspondence with the union of the proximal connection arm 41b with the two proximal hinging rings 41a, a proximal connection hole 41g whose function will be described hereafter.

Two slots are instead provided integral with the proximal hinging rings 41a, which are intended to receive a joint locking screw 41f. Tightening the screw will allow the two slots and the proximal hinging rings 41a integral with these to be brought closer together.

The distal joining portion 4b comprises a coupling element 42 and a distal connector 43 associated to it.

The coupling element 42 has a distal hinging ring 42a with an internal and an external diameter equal to those of the above-described proximal hinging rings 41a. A protuberance defining a sliding seat 42b for the distal connector 43 extends integral with the distal hinging ring 42a, having an axis that is substantially tangential to the distal hinging ring 42a. The sliding seat 42b has two lateral edges that can be fastened by means of a distraction blocking screw 42c.

The coupling element 42 shows, in correspondence with the union of the distal hinging ring 42a with the protuberance defining the sliding seat 42b, a distal connection hole 42g whose function will be described hereafter.

The distal connector 43 comprises a sliding arm 43a attached in an L-shaped connection to a distal connection arm 43b. The two arms foul an angle of about 114°.

The sliding arm 43a slides into the sliding seat 42b, where its axial movement is limited by an abutment surface. Through this abutment surface, however, passes a distraction control screw 43f, whose head emerges from the coupling element 42. The threaded shank of the distraction control screw 43f instead is engaged in a longitudinal hole of the sliding arm 43a, so that rotation of said screw promotes translation of the arm along the sliding seat 42b.

The operation of the distraction control screw 43f thus determines a translation of the distal anchoring means 3 with respect to the hinging axis x, in particular along a distraction axis y inclined by a distraction angle α with respect to the longitudinal axis z of the distal bone 101. Given the inclination of 114° between the two arms of the distal connector, the distraction angle α is approximately equal to 66°. The distraction control screw 43f thus defines appropriate joint distraction means 102.

A mechanical peg is provided to allow the distraction control screw 43f to be locked in position.

The free end of the distal connection arm 43b instead has an insertion seat 43c for the distal rod 39, 39", composed of a through-hole defined by the two edges of the distal connection arm 43b alongside each other. The two edges can be brought closer to each other by means of a distal connection screw 43d. The distal rod 39, 39", once inserted in the insertion seat 43c, is locked in position by tightening the distal connection screw 43d.

The hinge that allows the two joining portions 4a, 4b to be rotatably mounted is defined by the centering window 40 and by the three hinging rings 41a, 42a.

The two proximal hinging rings 41a are mounted integrally with the peripheral cylindrical surface of the centering window 40. The shoulder edge 40c of the centering window 40 abuts against a counter-shaped impression on one of the two rings, while the other ring is fixed by means of the four elastic fixing pegs 40d to the opposite end of the cylindrical surface.

The distal hinging ring 42a is inserted between the two proximal hinging rings 41a, slidingly rotatable around the peripheral cylindrical surface of the centering window 40 and advantageously having a thickness that is equal to the distance between the interaxial centers of the two proximal hinging rings 41a.

Given this structure, it is possible to rotate the distal joining portion 4b with respect to the proximal portion 4a by sliding the distal cylindrical ring 42a along the peripheral cylindrical surface of the centering window.

It should be noted that tightening the joint locking screw 41f allows the relative position of the two joining portions 4a, 4b, and accordingly of the anchoring means 2, 3 associated to these, to be fixed.

Moreover, by means of said distraction control screw 43f it is possible to adjust the distance of the axis of the distal rod 39, 39" with respect to the hinging axis x, thus performing the joint distraction. This adjustment can conveniently be blocked by tightening said distraction blocking screw 42c.

The articulator 4 described above has several advantages, first of, all the fact that it reproduces the movement of the elbow joint 102, thus ensuring enough stability to the joint itself and protecting it from overload.

The articulator 4 also considerably facilitates the delicate operation of centering the orthopaedic device, thanks to the radiotransparent centering window 40 with central tube 40a and radiopaque references 40b.

Moreover, as described above, the articulator can perform a joint distraction along the anatomical axis of access of the humerus to the joint itself, with an angle of 114°.

Thanks to the orientation of the distal connector 43, the orthopaedic device is connected to the ulna, and therefore not constrained by the position of the joint in that instant. Any possibility of error on the part of the surgeon during the implantation is removed.

The articulator 4 is also ambidextrous, necessitating only that one inserts the screws and attaches the closing nuts on the desired side.

Finally, the articulator 4 can advantageously be connected to an auxiliary device 5, 205.

In a first embodiment, which can be seen in FIGS. 16-20, the auxiliary device 5 is structured like a cylindrical box-shaped body 50 on which a plate-like rotating portion 51 (simply referred to as rotating plate) is rotatably engaged. The box-shaped body 50 has an eyelet 50a intended to receive a fixing screw to the articulator 4. Similarly, the rotating plate 51 comprises a protuberance that extends and cantilevers over the box-shaped body 50 below and that supports a fixing pin 52 for coupling to the articulator. The screw and the fixing pin 52 engage the above-identified connection holes 41g, 42g of the articulator 4.

Inside an internal hollow 57 of the box-shaped body 50 a toothed wheel 53 is arranged that is integrally connected to the rotating plate 51 by means of a drum 54 that passes through a guide hole on an upper surface of the box-shaped body 50.

The group consisting of the toothed wheel 53, drum 54 and rotating plate 51 is thus rotatably movable with respect to the box-shaped body 50. This group can be placed in two alternative positions, determining two different operational configurations of the auxiliary device 5. In a first configuration, the rotating plate 51 abuts against the upper surface of the box-shaped body; in a second configuration, this rotating plate 51 is instead lifted with respect to that same surface.

The toothed wheel 53 integral with the rotating plate 51 is thus in two axially separate positions within the internal hollow 57 when the operational configuration of the auxiliary device 5 changes. In the first operational configuration, the periphery of said toothed wheel 53 engages a worm screw 55 that passes through the box-shaped body 50 at the base of the eyelet 50a. In the second operational configuration, the toothed wheel 53 is on a far plane with respect to the plane of the worm screw 55 and idle with respect to the latter.

Three pressure elements 56 are conveniently arranged within the box-shaped body 50; they press radially against a shared peripheral groove 54a of the two grooves that are present on the drum 54 in order to respectively engage either the first or the second operational configuration of the auxiliary device 5.

A gripping handle 51a is also suitably arranged on the external surface of the rotating plate 51, which allows the operational configuration of the auxiliary device 5 to be easily changed. As an alternative to said gripping handle 51a it is possible to form a peripheral gripping profile on the rotating plate.

The two opposite ends of the worm screw 55 take the form of control heads 55a that emerge from the box-shaped body 50; by manipulating these control heads 55a it is possible to rotate the worm screw 55. In this manner it is possible, in the first operational configuration of the auxiliary device 5, to simultaneously promote the rotation of the toothed wheel 53 and the relative movement of the rotating plate 51 with respect to the box-shaped body 50. If the auxiliary device 5 is fixed to the articulator 4 in one of the manners described above, this relative movement results in a relative rotation of the two joining portions 4a, 4b, and accordingly in a change of the subtended angle between the proximal rod 29 and the distal one 39, 39".

Thus the worm screw 55, the toothed wheel 53 and the drum 54 define a mechanical reduction gear, whose input is represented by the control heads 55a and whose output is represented by the rotating plate 51. Advantageously, the gear ratio of the mechanical reduction gear is extremely low, so that, by acting on the control member defined by the control heads 55a when the auxiliary device 5 is in the first operational configuration, it is possible to perform a micrometric adjustment of the relative orientation of the anchoring means 2, 3 of the external orthopaedic fixator 1.

A plurality of limitation through-holes 51b arranged in the shape of a half-moon are present on the box-shaped body 50. By inserting an apposite limitation peg 51c, which passes through a slot on the rotating plate 51, in one of said holes, thanks to the presence of apposite limit stops inside the box-shaped body 50 it is possible to obtain a limitation of the angular movement allowed to the rotating plate 51 with respect to the box-shaped body 50. This limitation clearly results in a limitation of the relative orientation angle of anchoring means 2, 3 of the external orthopaedic fixator 1.

Near the limitation holes 51b a graduated scale is advantageously included, so that the surgeon can insert the limitation peg 51c in the limitation hole 51b that corresponds to the desired angle of joint limitation.

The limitation holes 51c are grouped in two series corresponding to the arms of the half-moon arrangement; by inserting a limitation peg 51c in one of the holes of the first series the angular movement of the auxiliary device is limited on the lower side, by inserting a limitation peg 51c in one of the holes of the second series the angle is instead limited on the upper side. Obviously, it is possible to insert a pin in both series to limit the angle on both the upper and the lower side.

Two housings intended to contain a number of limitation pegs 51c that are being used, are present in the body of the gripping handle 51a.

Figures 9, 10:
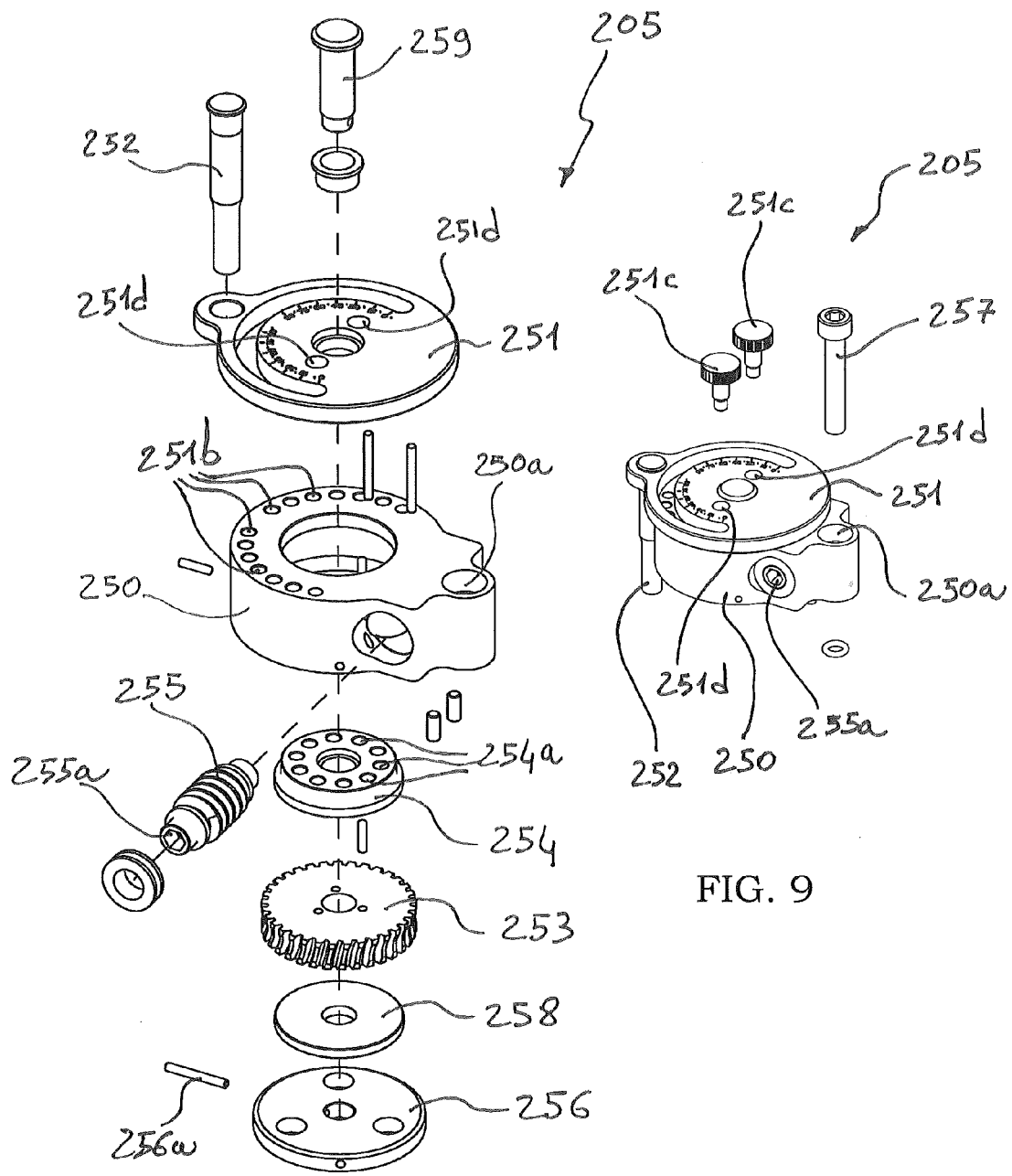
FIG. 9 is an axonometric view of an embodiment of an auxiliary device of the external orthopaedic fixator according to the invention.
FIG. 10 is an exploded view of the device of FIG. 9.

In a second alternative embodiment, which can be seen in FIGS. 9-10, the auxiliary device 205 is structured like a cylindrical box-shaped body 250 on top of which a plate-like rotating portion 251 (simply referred to as rotating plate) is rotatably engaged by means of a central pivot 259. The box-shaped body 250 has an eyelet 250a intended to receive a fixing screw 257 to the articulator 4. Similarly, the rotating plate 251 comprises a protuberance that extends and cantilevers over the box-shaped body 250 below and that supports a fixing pin 252 for coupling to the articulator. The screw 257 and the fixing pin 252 engage the above-identified connection holes 41g, 42g of the articulator 4.

Within the box shaped-body, a toothed wheel 253 and a drum 254 are arranged to form a common block; both the axes of the toothed wheel 253 and the drum 254 are aligned with the central pivot 259. The block is kept within the box-shaped body 250 by means of a cover 256. A disk-shaped spacer 258 is placed between the cover 256 and the toothed wheel 253. Three lateral pins 256a fix the cover to the box-shaped body 250.

The drum 254 has an upper portion with a smaller radius which is hosted in a guide hole on an upper surface of the box-shaped body 250; the upper portion of the drum 254 is then flush with the upper surface of the box-shaped body. The upper portion of the drum 254 exhibits a plurality of threaded holes 254a, opening on its top and arranged in a circular fashion along a periphery of the drum 254.

The rotating plate 251 exhibits two blocking through-holes 251d placed on opposite sides of the central pivot 259. Two of the threaded holes 254a of the drum 254 may be aligned with the two blocking through-holes 251d.

The auxiliary device 205 comprises two limitation pegs 251c having a handle and a shaft provided with a threaded end. The limitation pegs 251a may be inserted in the blocking through-holes 251d of the rotating plate 251 and screwed in the threaded holes 254a of the drum 254. In this way, the block consisting of the toothed wheel 53 and the drum 54 is rendered integral with the rotating plate 51.

When the limitation pegs 251c are screwed in the blocking through-holes 251d blocking the rotating of the plate 251 with respect to the drum 254, the auxiliary device 205 is in a first operational configuration; when the limitation pegs 251c are not inserted in the blocking through-holes 251d, the rotating plate 251 is freely rotatable with respect to the drum; in this latter case the auxiliary device 205 is in a second operational configuration.

The periphery of the toothed wheel 253 engages a worm screw 255 that passes through the box-shaped body 250 next to the eyelet 250a.

The two opposite ends of the worm screw 255 take the form of control heads 255a that emerge from the box-shaped body 250; by engaging these control heads 255a with a corresponding tool it is possible to rotate the worm screw 255. By rotating the toothed wheel 253 the drum 254 is also put in rotation.

When the auxiliary device 205 is in its first operational configuration, the rotating plate 251 rotates with the drum 254 and changes its position with respect to the box-shaped body 250. If the auxiliary device 205 is fixed to the articulator 4 in one of the manners described above, this relative movement results in a relative rotation of the two joining portions 4a, 4b, and accordingly in a change of the subtended angle between the proximal rod 29 and the distal one 39, 39".

Thus the worm screw 255, the toothed wheel 253 and the drum 254 define a mechanical reduction gear, whose input is represented by the control heads 255a and whose output is represented by the rotating plate 251. Advantageously, the gear ratio of the mechanical reduction gear is extremely low, so that by manipulating the control member defined by the control heads 255a when the auxiliary device 205 is in the first operational configuration, it is possible to perform a micrometric adjustment of the relative orientation of the anchoring means 2, 3 of the external orthopaedic fixator 1.

On the contrary, when the auxiliary device 205 is in its second operational configuration, the drum 254 rotates freely with respect to the rotating plate 251 and an action on the control heads 255a has no effect on the anchoring means 2, 3 orientation.

A plurality of limitation through-holes 251b arranged in the shape of a half-moon is present on the box-shaped body 250. When inserting one of the limitation pegs 251c, which passes through a slot on the rotating plate 251, into one of limitation through-holes 251b, the presence of apposite stops inside the box-shaped body 250 make is possible to obtain a limitation of the angular movement allowed to the rotating plate 251 with respect to the box-shaped body 250. This limitation clearly results in a limitation of the relative orientation angle of the anchoring means 2, 3 of the external orthopaedic fixator 1. Near the limitation holes 251b a graduated scale is advantageously included, so that the surgeon can insert the limitation peg 251c in the limitation hole 251b that corresponds to the desired angle of joint limitation.

The limitation holes 251c are grouped in two series corresponding to the arms of the half-moon arrangement; by inserting a limitation peg 251c in one of the holes of the first series, the angular movement of the auxiliary device is limited on the lower side, by inserting a limitation peg 251c in one of the holes of the second series, the angle is instead limited on the upper side. Obviously, it is possible to insert a pin in both series to limit the angle on both the upper and the lower side.

Of course, the limitation pegs 251c may be employed in order to limit the angular range of the device only when they are not employed to secure the rotating plate 251 on the drum 254, i.e. only in the second configuration of the auxiliary device 205.

Figure 21:
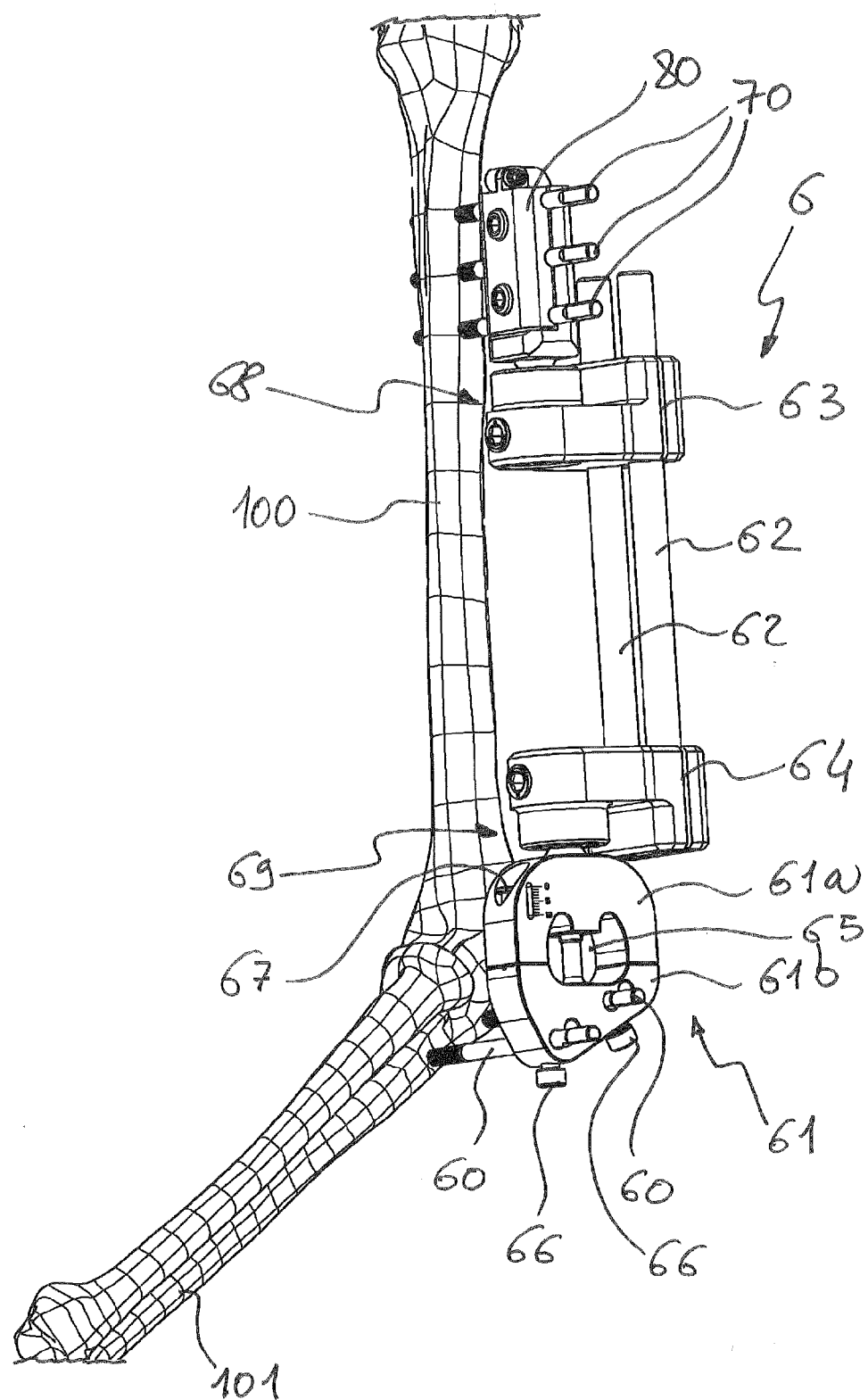
FIG. 21 is a view of a distraction device associated to an elbow joint.

The external orthopaedic fixator 1 according to the present invention can be advantageously implanted after having performed a joint distraction through a distraction device 6 which can be seen in FIG. 21 and which is briefly described hereafter.

The distraction device 6 comprises a proximal clamp 80 that engages itself on the humerus by means of three endosseous pins 70, and a distal clamp 61 that engages itself on the ulna by means of two distal pins 60. Endosseous pins may be used in the subsequent steps of the operation to apply the external orthopaedic fixator 1.

The distal clamp 61 comprises a fixed portion 61b and a telescopically movable portion 61a that moves with respect to the first one. The fixed portion 61b can be firmly anchored to the patient's ulna 101 by means of the two distal pins 60 that are inserted in two bilobate through-holes of the element. Said distal pins 60 are kept in position inside said holes by means of two blocking screws 66.

The telescopic movement of the movable portion 61a can be adjusted by means of a distraction screw 67.

The two portions of the distal clamp are both convex at their reciprocal connection points, so that they define a centering window 65 that opens onto the elbow joint and that is helpful in properly centering the distraction device 6.

The proximal clamp 80 is associated, by means of a first ball joint 68, to a first connection element 63 to which a pair of parallel rods 62 is fixed in an axially adjustable way. The opposite end of the pair of rods 62 is fixed onto a second connection element 64, which is associated by means of a second ball joint 69 to the movable portion 61a of the distal clamp.

The telescopic movement of the distal clamp 61 allows the desired distraction to be performed in case of joint rigidity, along a fixed axis that is inclined by an angle α (preferably 70°) with respect to the ulna 101.

The invention claimed is:

1. An external orthopaedic fixator for elbow joints comprising:
    a proximal anchoring member intended to be integrally associated to a proximal bone of a patient's upper limb;
    a distal anchoring member intended to be integrally associated to a distal bone of a patient's upper limb;
    a joint distraction member for distraction control to allow the distal anchoring member to be translated with respect to the proximal anchoring member;
    an articulator that hinges said proximal anchoring member to said distal anchoring member along a hinging axis, intended to be positioned in correspondence with an elbow joint connecting said proximal and distal bones, said articulator comprising a radiotransparent centering window intended to frame the elbow joint when positioning the external orthopaedic fixator, said hinging axis passing through said centering window, said articulator also comprising a proximal joining portion which is associated to the proximal anchoring member and a distal joining portion which is associated to the distal anchoring member, wherein said distal joining portion comprises a coupling element hinged to the proximal joining portion and a distal connector integral with the distal joining portion and slidably movable with respect to the coupling element, said joint distraction member being arranged to promote the translation of the distal connector with respect to the coupling element of the articulator, and wherein said distal connector comprises a sliding arm that is slidably inserted into a sliding seat of the coupling element, said joint distraction member having the form of a distraction control screw comprising a head that is rotatably associated to the sliding seat and a shank engaged in the sliding arm;
    wherein said centering window comprises a central tube oriented along the hinging axis, for the potential insertion of a reference wire;
    wherein said proximal anchoring member comprises at least one proximal rod connected to the articulator and fixable to the proximal bone by means of proximal endosseous pins supported by at least one proximal clamp, said at least one proximal clamp comprising a first coupling element, arranged to lock the proximal endosseous pins, and a second coupling element arranged to lock the proximal rod, said first and second coupling elements being articulated with each other by means of an articulation pin comprising a head associated to the first coupling element and a shank associated to the second coupling element;
    wherein said second coupling element is selectively rotatable around the axis of said articulation pin; and
    wherein said head of the articulation pin has a through-hole through which an eccentric passes that is transverse to the first coupling element, said articulation pin being selectively rotatable with respect to said eccentric.

2. The external orthopaedic fixator according to claim 1, wherein said centering window has radiopaque references arranged to guide the centering of the elbow joint.

3. The external orthopaedic fixator according to claim 1, wherein said distal anchoring member comprises at least one distal rod connected to the articulator and fixed to the distal bone by means of distal endosseous pins which are directly supported by the distal rod and kept in position by means of locks that can be fastened to the distal rod through a fixing screw.

4. The external orthopaedic fixator according to claim 3, wherein said distal rod and said locks have opposite hollows that combine to define seats for the distal endosseous pins.

5. The external orthopaedic fixator according to claim 1, wherein said centering window has a cylindrical geometry whose center is the center of rotation for the proximal joining portion and the distal joining portion.

6. The external orthopaedic fixator according to claim 5, wherein one of said proximal or distal joining portions comprises at least one hinging ring rotatably slidable along an external cylindrical periphery of the centering window, said centering window being integral with the other joining portion.

7. The external orthopaedic fixator according to claim 6, wherein said articulator comprises a joint locking member arranged to block the relative rotation between the proximal joining portion and the distal joining portion.

8. The external orthopaedic fixator according to claim 1, wherein said translation occurs along a distraction axis that is inclined by an angle of distraction with respect to the longitudinal axis of the distal bone, said angle of distraction being comprised between 60° and 75°.

9. An external orthopaedic fixator for elbow joints comprising:
    a proximal anchoring member intended to be integrally associated to a proximal bone of a patient's upper limb;
    a distal anchoring member intended to be integrally associated to a distal bone of a patient's upper limb;
    a joint distraction member for distraction control to allow the distal anchoring member to be translated with respect to the proximal anchoring member;
    an articulator that hinges said proximal anchoring member to said distal anchoring member along a hinging axis, intended to be positioned in correspondence with an elbow joint connecting said proximal and distal bones, said articulator comprising a radiotransparent centering window intended to frame the elbow joint when positioning the external orthopaedic fixator, said hinging axis passing through said centering window, said articulator also comprising a proximal joining portion which is associated to the proximal anchoring member and a distal joining portion which is associated to the distal anchoring member, wherein said distal joining portion comprises a coupling element hinged to the proximal joining portion and a distal connector integral with the distal joining portion and slidably movable with respect to the coupling element, said joint distraction member being arranged to promote the translation of the distal connector with respect to the coupling element of the articulator, and wherein said distal connector comprises a sliding arm that is slidably inserted into a sliding seat of the coupling element, said joint distraction member having the form of a distraction control screw comprising a head that is rotatably associated to the sliding seat and a shank engaged in the sliding arm;

wherein said distal connector comprises a distal connection arm intended to longitudinally receive a distal rod of the distal anchoring member, the subtended angle between the sliding arm and the distal connection arm being comprised between 105° and 120°.

10. The external orthopaedic fixator according to claim 9, further comprising a distraction blocking member arranged to block the relative translation between the distal anchoring member and the proximal anchoring member.

11. An external orthopaedic fixator for elbow joints comprising: a proximal anchoring member intended to be integrally associated to a proximal bone of a patient's upper limb; a distal anchoring member intended to be integrally associated to a distal bone of a patient's upper limb; a joint distraction member for distraction control to allow the distal anchoring member to be translated with respect to the proximal anchoring member; an articulator that hinges said proximal anchoring member to said distal anchoring member along a hinging axis, intended to be positioned in correspondence with an elbow joint connecting said proximal and distal bones, said articulator comprising a radiotransparent centering window intended to frame the elbow joint when positioning the external orthopaedic fixator, said hinging axis passing through said centering window, said articulator also comprising a proximal joining portion which is associated to the proximal anchoring member and a distal joining portion which is associated to the distal anchoring member, the external orthopedic fixator further comprising an auxiliary device that is coupled with the articulator and that allows the relative rotation between the proximal and distal joining portions to be micrometrically adjusted, wherein said auxiliary device comprises a box-shaped body, a rotating portion that is rotatably associated to said box-shaped body, and a fixing member intended to fix the box-shaped body and the rotating portion to the proximal joining portion and to the distal joining portion respectively or vice versa; said box-shaped body comprising a mechanical reduction gear intended to transmit a rotational movement from a control member to the rotating portion, said mechanical reduction gear being housed inside said box-shaped body;

wherein said auxiliary device has two alternative configurations, a first configuration wherein said rotating portion is coupled to said control member by means of said mechanical reduction gear, and a second configuration wherein said rotating portion is idle with respect to said control member;

wherein a drum integral with a toothed wheel, is selectively coupled to the rotating portion by means of at least one limitation peg; and comprising a plurality of limitation holes on the rotating portion intended to house the at least one limitation peg, said at least one limitation peg interacting with limit stops of the box-shaped body for selectively limiting the angular excursion allowed between the box-shaped body and the rotating portion.

* * * * *